(12) United States Patent
Faatz et al.

(10) Patent No.: US 7,094,757 B2
(45) Date of Patent: Aug. 22, 2006

(54) COMPLEXES COMPRISING A PRION PROTEIN AND A PEPTIDYL PROLYL ISOMERASE CHAPERONE, AND METHOD FOR PRODUCING AND USING THEM

(75) Inventors: Elke Faatz, Huglfing (DE); Christian Scholz, Penzberg (DE); Werner Stock, Graefelfing (DE); Peter Schaarschmidt, Uffing (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 274 days.

(21) Appl. No.: 10/745,393

(22) Filed: Dec. 23, 2003

(65) Prior Publication Data

US 2004/0203131 A1    Oct. 14, 2004

Related U.S. Application Data

(63) Continuation-in-part of application No. 10/179,905, filed on Jun. 24, 2002, which is a continuation-in-part of application No. 10/167,774, filed on Jun. 10, 2002, now abandoned.

(30) Foreign Application Priority Data

Jun. 22, 2001   (EP) .............................................. 01115225
Aug. 31, 2001   (EP) .............................................. 01120939

(51) Int. Cl.
C07K 14/00   (2006.01)
C12N 9/00   (2006.01)

(52) U.S. Cl. ...................... 514/12; 435/183; 435/320.1; 530/350

(58) Field of Classification Search ...................... 514/2; 530/350; 435/183, 320.1; 536/23.1
See application file for complete search history.

(56) References Cited

U.S. PATENT DOCUMENTS

| | | | |
|---|---|---|---|
| 4,735,896 A | 4/1988 | Wang et al. ..................... | 435/5 |
| 4,879,212 A | 11/1989 | Wang et al. ..................... | 435/5 |
| 4,945,042 A | 7/1990 | Geiger et al. | |
| 5,908,626 A | 6/1999 | Chang et al. | |
| 5,942,252 A | 8/1999 | Tice et al. | |
| 6,207,420 B1 | 3/2001 | Harrison et al. | |
| 6,316,405 B1 | 11/2001 | Rich et al. | |

FOREIGN PATENT DOCUMENTS

| | | |
|---|---|---|
| AU | 597884 | 4/1986 |
| EP | 0 061 888 | 10/1982 |
| EP | 0 293 249 B1 | 8/1992 |
| EP | 0 280 211 B1 | 11/1994 |
| EP | 0 396 559 B1 | 8/1996 |
| EP | 1 077 262 | 2/2001 |
| WO | WO 92/22573 | 12/1992 |
| WO | WO 93/21346 | 10/1993 |
| WO | WO 93/25533 | 12/1993 |
| WO | WO 94/08012 | 4/1994 |
| WO | WO 97/10253 | 3/1997 |
| WO | WO 98/01349 | 1/1998 |
| WO | WO 98/13496 | 1/1998 |
| WO | WO 00/20606 | 4/2000 |
| WO | WO 00/26251 | 5/2000 |
| WO | WO 00/28011 | 5/2000 |

OTHER PUBLICATIONS

Stockton et al. Nov. 11, 2003; Biochemistry 42:12821–12834.*
Aslam, M. and Dent, A., The preparation of protein–protein conjugates in "Bioconjugation", eds. M. Aslam and A. Dent, McMillan Reference, London (1998), pp. 216–363.
Bardwell, J., *Building Bridges: Disulphide Bond Formation in the Cell*, Molecular Microbiology (1994) 14(2), 199–205.
Beissinger, M., et al., *How Chaperones Fold Proteins, Biol. Chem.*, vol. 379, pp. 245–259, Mar. 1998.
Bothmann, H., et al., *The Periplasmic Escherichia coli Peptidylprolyl cis,trans–Isomerase FkpA*, The Journal of Biological Chemistry, vol. 275, No. 22, Issue of Jun. 2, pp. 17100–17105, 2000.
Braden, B.C., and Poljak, R.J., Faseb J. 9 (1995) 9–16.
Buchner, J., *Supervising The Fold: Functional Principles of Molecular Chaperones*, The Faseb Journal, pp. 10–19, vol. 10, Jan. 1996.
Butler, J.E., et al., *The Physical and Functional Behavior of Capture Antibodies Adsorbed on Polystyrene*, Journal of Immunological Methods, 150 (1992), 77–90.
Caffrey, M., et al., *Biophysical Characterization of gp41 Aggregates Suggests a Model for the Molecular Mechanism of HIV–Associated Neurological Damage and Dementia*, The Journal of Biological Chemist, vol. 275, No. 26, Issue of Jun. 30, pp. 19877–19882, 2000.
Chan, D., et al., *Core Structure of gp41 From The HIV Envelope Glycoprotein*, Cell, vol., 89, 263–273, Apr. 18, 1997.
Colowick, S.P., and Caplan, N.O., Methods in Enzymology, Academic Press (1980).
Crooke, E., and Wickner, W., Proc. Natl. Acad. Sci. USA 84 (1987) 5216–5220.
Danese, P.N., et al., Genes Dev. 9 (1995) 387–398.
Dartigalongue, C., and Raina, S., Embo J. 17 (1998) 3968–3980.
Dent, A., et al., *The Preparation of Protein–Protein Conjugates*, Heterobifunctional Reagents Based on the Biotin–Avidin Interaction, Chapter 5, pp. 261–363.
Doms, R., et al., *HIV–1 Membrane Fusion: Targets of Opportunity*, The Journal of Cell Biology, pp. F9–F13. vol. 151, No. 2, Oct. 16, 2000.

(Continued)

*Primary Examiner*—Karen Cochrane Carlson
(74) *Attorney, Agent, or Firm*—Brinks Hofer Gilson & Lione

(57) ABSTRACT

The present invention relates to the diagnosis of transmissible spongiform encephalopathies (TSEs). It especially teaches the production of a soluble prion protein (PrP)-chaperone complex and the advantageous use of such chaperone-PrP complex, especially in the detection of PrP in an immunoassay, as well as its use as and immunogen.

65 Claims, 5 Drawing Sheets

OTHER PUBLICATIONS

Figure 1:
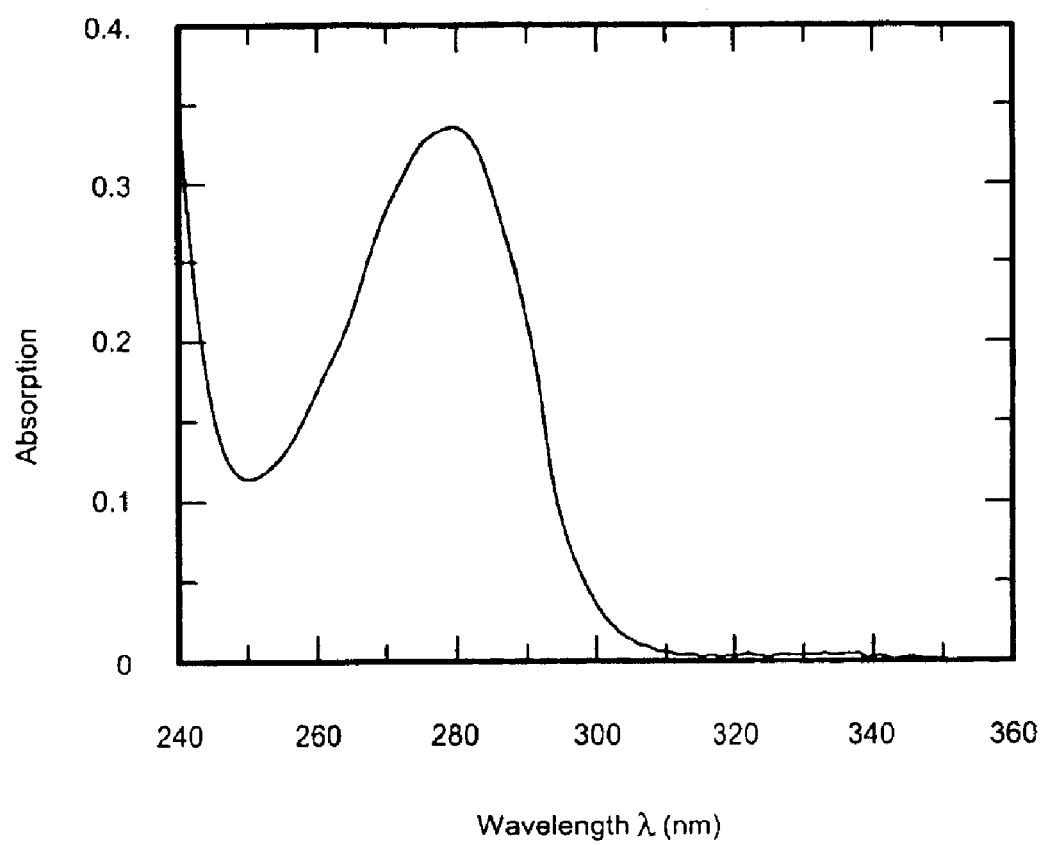
Figure 2:
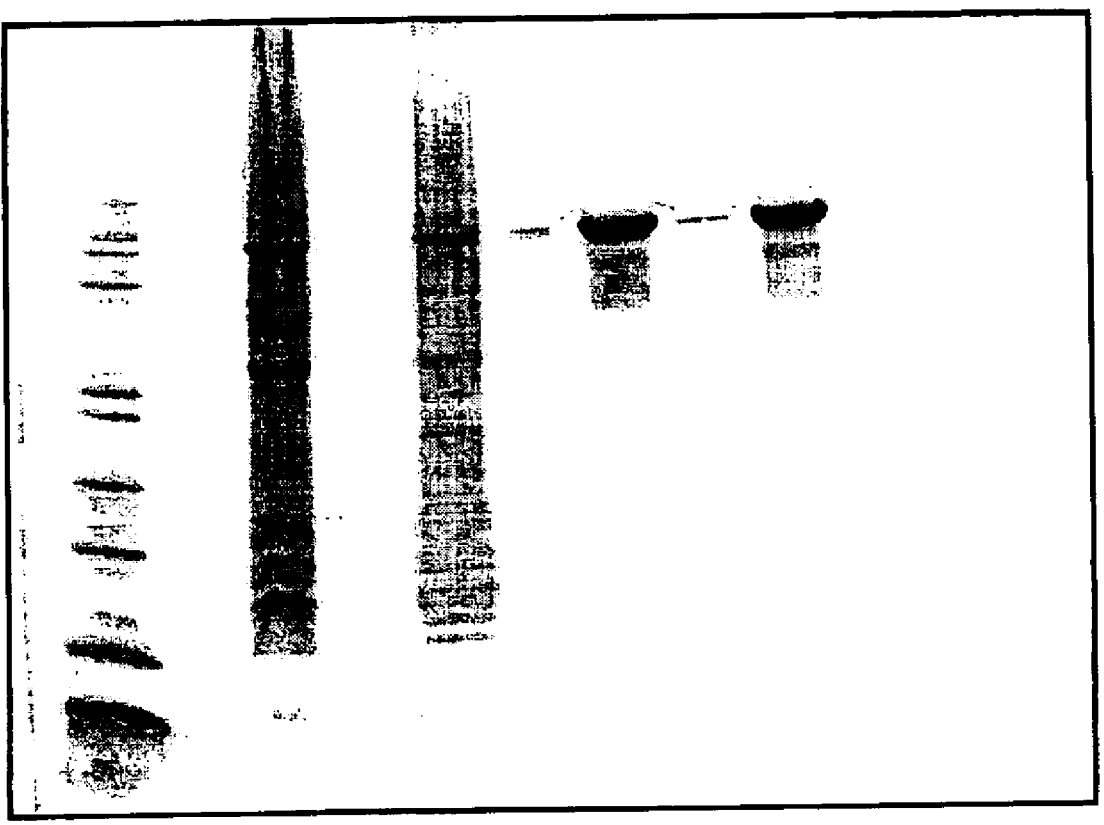
Figure 3:
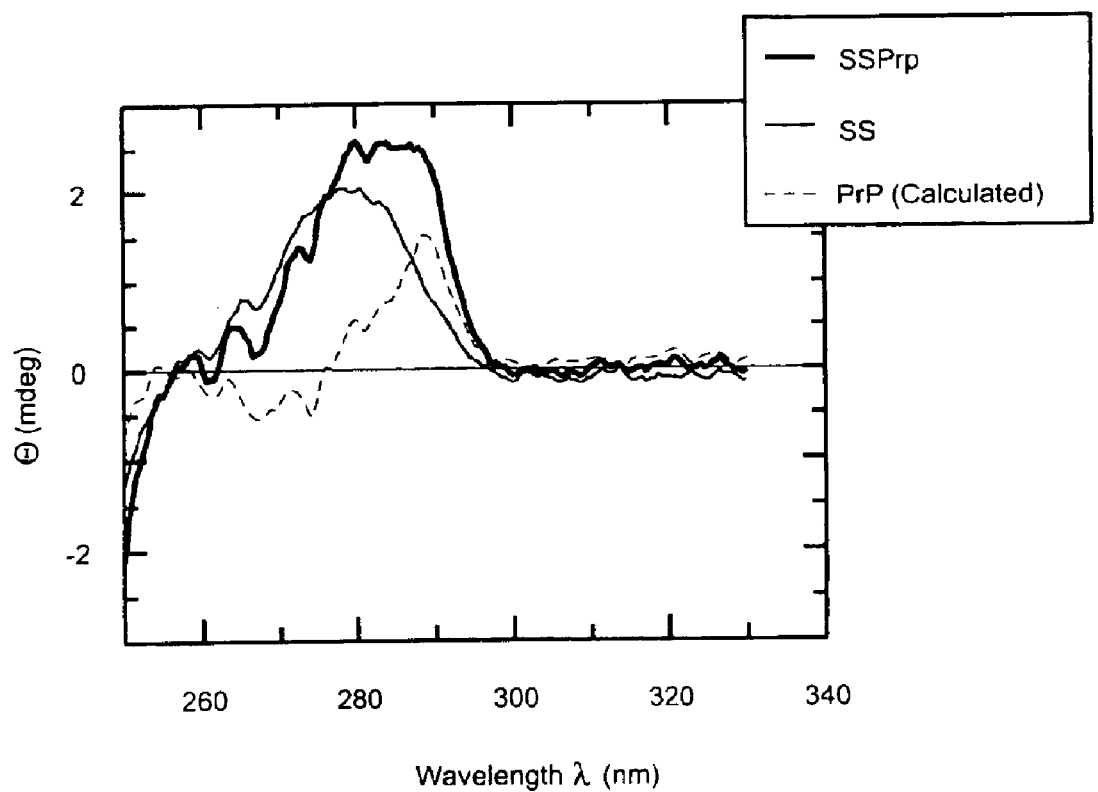
Figure 4A:
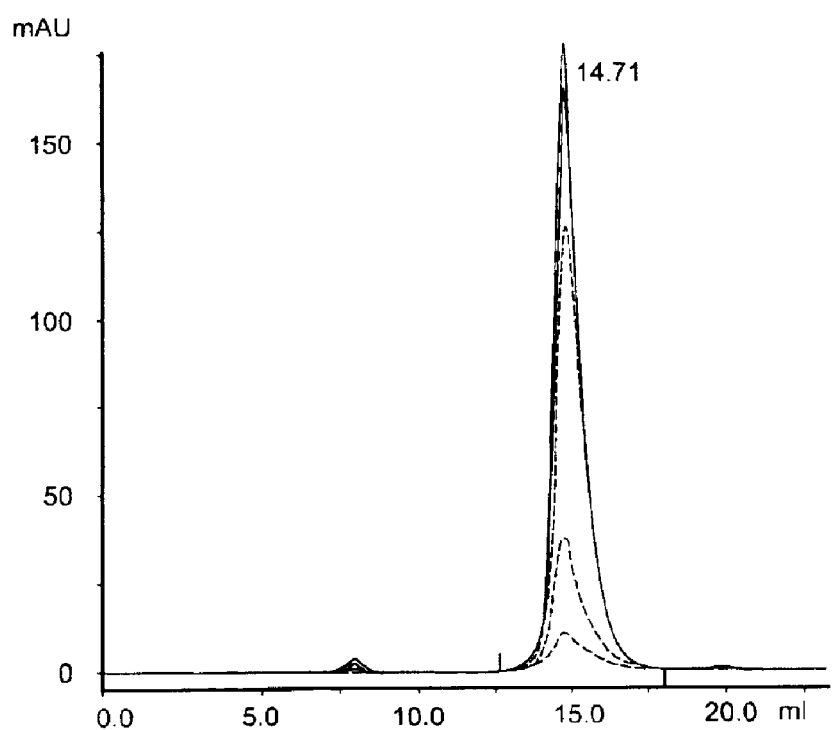
Figure 4B:
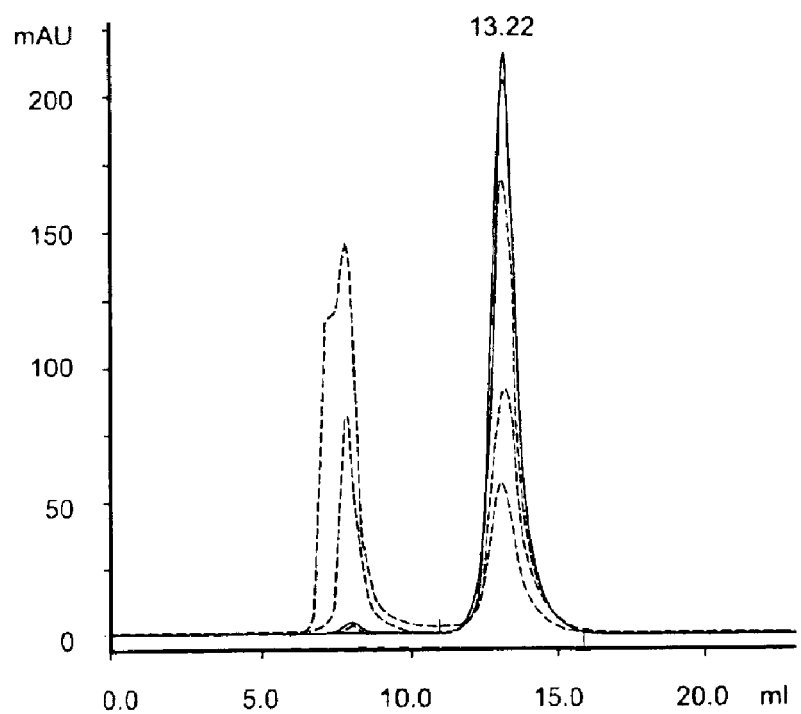

Ehrnsperger, Monika, et al., Stabilization of Proteins and Peptides in Diagnostic Immunological Assays by the Molecular Chaperone Hsp25, Analytical Biochemistry 259 (1998), pp. 218–225.

Egan, D.A., et al., Biochemistry 32 (1993) 1920–1927.

Endrich, et al., *The V3 Loop of Human Immunodeficiency Virus Type–1 Envelope Protein is a High–Affinity Ligand for Immunophilins Present in Human Blood*, Eur. J. Biochem., 252–441–446 (1998).

Fischer, G., et al., Nature 337 (1989) 476–478.

Frech, C., et al. *Preferential Binding of an Unfolded Protein to DsbA*, The EMBO Journal, vol. 15, No. 2, pp. 392–398, 1996.

Gething, M., *Protein Folding in the Cell*, Nature, vol. 355 Jan. 2, 1992.

Glenner, G.G., and Wong, C.W., Biochem. Biophys. Res. Commun. 120 (1984) 885–890.

Glenner, G.G., and Wong, C.W., Biochem. Biophys. Res. Commun. 122 (1984) 1131–1135.

Goethel, S.F., et al., *Peptide–Prolyl Cis–Trans Isomerases, a Superfamily of Ubiquitous Folding Catalysts*, Cellular and Molecular Life Sciences (CMLS), pp. 423–436, vol. 55, 1999.

Guyader, M., et al., *Genome Organization and Transactivatioin of the Human Immunodeficiency Virus Type 2*, Nature, vol. 326 Apr. 16, 1987.

Hornemann, S., et al., FEBS Lett. 413 (1997) 277–281.

Hottenrott, S., et al., J. Biol. Chem. 272 (1997) 15697–15701.

Iwatsubo, T., et al., Neuron 13 (1994) 45–53.

Ivery, M.T.G., Immunophilins: Switched on Protein Binding Domains? Med Res Rev., Nov. 2000, pp. 452–484.

Kang, J., et al., Nature 325 (1987) 733–736.

Kay, J.E., Biochem J. 314 (1996) 361–385.

Kojouharova, M.S., et al., *Differential Binding of IgG and of a HIV gp41 Peptide by the B Chain and A Chain Globular Head Sequences of C1q, Respectively*, Journal of Immunology, 161:4352–4331.

Lane, W.S., *Complete Amino Acid Sequence of the FK506 and Rapamycin Binding Protein, FKBP, Isolated from Calf Thymus*, Journal of Protein Chemistry, pp. 151–160, vol. 10, No. 2, 1991.

Lu, Min., et al., *A Trimeric Structural Domain of the HIV–1 Transmembrane Glycoprotein*, Nature Structural Biology, pp. 1–8, vol. 2, No. 12, Dec. 1995.

Masters, C.L., et al., Proc. Natl. Acad. Sci. USA 82 (1985) 4245–4249.

Matsubara, Etsuro, et al., *Apolipoprotein J and Alzheimer's Amyloid β Solubility*, Biochem J. 316 (1996), pp. 671–679.

Meister, S., et al., *Basic Amino Acid Residues in the V3 Loop of Simian Immunodificiency Virus Envelope Alter Viral Coreceptor Tropism and Infectivity but Do Not Allow Efficient Utilization of CXCR4 as Entry Cofactor*, VIROLOGY, 284, 287–296 (2001).

Missiakas, D., et al., *Identification and Characterization of a New Disulfide Isomerase–Like Protein (DsbD) in Escherichia Coli*, The EMBO Journal, vol. 14, No. 14, pp. 3415–3424, 1995.

Missiakas, D., et al., *New Components of Protein Foling in Extracytoplasmic Compartments of Escherichia coli SurA, FkpA and Skp/OmpH*, Molecular Microbiology, (1996) 21(4), pp. 871–884.

Otteken, et al. *Calreticulin Interacts With Newly Synthesized Human Immunodeficiency Virus Type 1 Envelope Glycoprotein, Suggesting A Chaperone Function Similar to That of Calnexin*, The Journal of Biological Chemistry, vol. 271, No. 1, Jan. 5, 1996, pp. 97–103.

Pennisi, Elizabeth, Expanding the Eukaryote's Cast of Chaperones, Science, vol. 274, Dec. 1996 pp. 1613–1614.

Prusiner, S.B., *Prions*, Nobel Lecture, vol. 95, pp. 13363–1383, Nov. 1998.

Rahfeld, J., et al., *Confirmation of the Existence of a Third Family Among Peptidyl–Prolyl Cisltrans Isomerases Amino Acid Sequence and Recombinant Production of Parvulin*, FEBS Letters, 352 (1994) pp. 180–184.

Ramm, K., et al., *The Periplasmic Escherichia coli Peptidylprolyl Cis, Trans–Isomerase FkpA*, The Journal of Biological Chemistry, vol., 275, No. 22, Issue of Jun. 2, pp. 17106–17113, 2000.

Ratner, L., et al., *Complete Nucleotide Sequence of the AIDS Virus, HTLV–III*, NATURE, pp. 277–284, vol. 313, Jan. 24, 1985.

Roher, A.E., et al., Proc. Natl. Acad. Sci. USA 90 (1993) 10836–10840.

Root, M.J., et al., *Protein Design of an HIV–1 Entry Inhibitor*, SCIENCE, pp. 884–888, vol., 291, Feb. 2, 2001.

Schmid, F. X., Molecular chaperones in the life cyle of proteins, eds. A.L. Fink and Y. Goto, Marcel Decker Inc., New York (1998), pp. 361–389.

Scholz, C., et al., Embo J. 16 (1997) 54–58.

Scholz, C., et al., J. Biol. Chem. 271 (1996) 12703–12707.

Selkoe, D.J., et al., J. Neurochem. 46 (1986) 1820–1834.

Selkoe, D.J., J. Neuropath. and Exp. Neurol. 53 (1994) 438–447.

Selkoe, D.J., Neuron 6 (1991) 487.

Speth, C., et al., *A 60 kD Heat–Shock Protein–Like Molecule Interacts with the HIV Transmembrane Glycoprotein gp41*, Molecular Immunology, 36 (1999) 619–628.

Stoller, G., et al., Embo J. 14 (1995) 4939–4948.

SWISS–PROT, accession No. P 45523.

Tijssen, In: "Methods in Enzymology", eds. S.P. Colowick, N.O. Caplan, Academic Press (1980).

Tijssen, P., Preparation of enzyme–antibody or other enzyme–macromolecule conjugates, In: "Practice and theory of enzyme immunoassays", eds. R.H. Burdon and v. P.H. Knippenberg, Elsevier, Amsterdam (1990), pp. 221–278.

Wang, C., et al., *Protein Disulfide Isomerase is Both an Enzyme and a Chaperone*, The FASEB Journal, vol. 7, pp. 1515–1517, Dec. 1993.

White, C., et. al, Nature 422 (2003) 80–83.

Wild, C., et al., *A Synthetic Peptide Inhibitor of Human Immunodeficiency Virus Replication: Correlation Between Solution Structure and Viral Inhibition*, Proc. Natl. Acad. Sci., vol. 89, pp. 10537–10541, Nov. 1992.

Wingfield, P.T., et al., *The Extracellular Domain of Immunodeficiency Virus gp41 Protein: Expression in Escherichia coli, Purification, and Crystallization*, Protein Science, p. 1653–1660 (1997).

Winter, J., *Increases Production of Human Proinsulin in the Periplasmic Space of Escherichia coli by Fusion to DsbA*, Journal of Biotechnology, 84 (2000) 175–185.

Yang, Yunning, et al., Communication The Chaperone BiP/GRP78 Binds to Amyloid Precursor Protein and Decreases Aβ40 and Aβ42 Secretion, The Journal of Biological Chemistry, vol. 273, No. 40, Oct. 1998, pp. 25552–25555.

Zahn, R., et al., FEBS Lett. 417 (1997) 400–404.

Zarnt, T., et al., *Molecular Structure on the Trigger Factor Required for High Activity in Protein Funding*, Journal of Molecular Biolology (1997), 271, 827–837.

* Ausubel, F.M. (Editor), et al., Current Protocols in Molecular Biology, vol. 3, 2001.

Beaucage., S.L., et al., *Deoxynucleoside Phosphoramidites—A New Class of Key Intermediates for Deoxypolynucleotide Synthesis*, Department of Chemistry, University of Colorado, pp. 1859–1862.

Ellis, R.W. (Chapter 29 of "VACCINES", 64(1):363–365, 1996.

Herbert et al. eds, *The Dictionary of Immunology*, Academic Press, 1995.

Kapust, R.B., et al., *Escherichia coli Maltose–Binding Protein is Uncommonly Effective at Promoting the Solubility of Polypeptides to Which it is Fused*, Protein Science (1999), pp. 1668–1674.

Kohda et al., *Biochemical Engineering Journal*, 10:39–45, 2002; see abstract and discussion.

Maniatis, T., et al., *Molecular Cloning, A Laboratory Manual*, Cold Spring Harbor Laboratory, 1982, Table of Cotents, Seven Pages.

Matteucci, M.D., et al., *Synthesis of Deoxyoligonucleotides on a Polymer Support*, Journal of The American Chemical Society, vol. 103, No. 11, 1981.

Metzger D., et al., *The Human Oestrogen Receptor Functions in Yeast*, Nature, pp. 31–316, vol. 334, Jul. 7, 1988.

Nishihara K. et al., "Overexpression of Trigger Factor Prevents Aggregation of Recombinant Proteins in *Escherichia coli*," Applied and Environmental Microbiology (Mar. 2000) 66(3):884–889.

Spreng S. and Gentschev I., "Construction of Chromosomally Encoded Secreted Hemolysin Fusion Proteins By Use of Mini–TnhlyA$_s$ Transposon," *FEMS Microbiology Letters* (1998) 165:187–192.

Schein C., "Production of Soluble Recombinant Proteins in Bacteria," *Biotechnology Nature* (Nov. 1989) 7(11): 1141–1149.

Weir, et al., *Handbook of Experimental Immunology*, vol. 1: Immunochemistry, p. 8.14–8.15.

* cited by examiner

COMPLEXES COMPRISING A PRION PROTEIN AND A PEPTIDYL PROLYL ISOMERASE CHAPERONE, AND METHOD FOR PRODUCING AND USING THEM

RELATED APPLICATIONS

This application is a continuation-in-part of application Ser. No. 10/179,905, filed on Jun. 24, 2002, and entitled "Soluble Complexes of Target Proteins and Peptidyl Prolyl Isomerase Chaperones and Methods of Making and Using Them," which claims the benefit of application Ser. No. 10/167,774, filed on Jun. 10, 2002 and now abandoned. Priority is also claimed, under 35 U.S.C. § 119 to EPO applications: EPO 01115225.3, filed on Jun. 22, 2001 and EPO 01120939.2, filed on Aug. 31, 2001. The disclosures of the priority applications are incorporated by reference herein in their entireties

BACKGROUND

1. Technical Field

The present invention relates to the diagnosis of transmissible spongiform encephalopathies (TSEs). It especially teaches the production of a soluble prion protein (PrP)-chaperone complex and the advantageous use of such chaperone-PrP complex, especially in the detection of PrP in an immunoassay, as well as its use as an immunogen.

2. Background Information

Transmissible spongiform encephalopathies (TSEs) include kuru-kuru, Creutzfeldt-Jakob disease (CJD), Gerstmann-Sträussler-Scheinker syndrome (GSS) and fatal familial insomnia (FFI) in humans, bovine spongiform encephalopathy (BSE), and scrapie in sheep. It is believed that the TSEs are caused by a novel class of infectious pathogens the so-called prion proteins or prions. According to the protein-only hypothesis the "infectious agent" is the prion protein in an abnormal oligomeric form which is called prion protein scrapie type (=$PrP^{Sc}$). The mammalian prion protein is highly conserved during evolution and normally is a monomeric cell surface glycoprotein which is termed $PrP^C$, wherein $^C$ stands for cellular. Both isoforms share the same amino acid sequence but differ in their secondary and tertiary structure. It is believed, that only the $PrP^{Sc}$ can transmit the disease, whereas $PrP^C$ appears not to be correlated with any disease mechanism leading to TSE.

Bovine spongiform encephalopathy (BSE) is a fatal, neuro degenerative, transmissible brain disease of cattle. The disease is fatal for cattle within weeks to months of its onset.

BSE first came to the attention of the scientific community in November 1986 with the appearance in cattle of a newly recognized form of neurological disease in the United Kingdom. Between November 1986 and November 2002, about 180 000 cases of BSE were confirmed in the United Kingdom.

Since 1989, when the first BSE case was reported outside the United Kingdom, relatively small numbers of cases (about 1500 in total) have also been reported in native cattle in many European countries and Japan. However, all but a couple of dozen have been reported in four countries—France, Ireland, Portugal and Switzerland.

Small numbers of cases have also been reported in Canada, the Falkland Islands, and Oman, but solely in animals imported from the United Kingdom.

Creutzfeldt-Jakob disease (CJD) is a rare and fatal neurodegenerative disease of unknown cause. Patients are usually aged between 50 and 75 and typical clinical features include a rapidly progressive dementia associated myoclonus and a characteristic electroencephalographic pattern. Neuropathological examination reveals cortical spongiform change, hence the term "spongiform encephalopathy".

H. G. Creutzfeldt is credited with the first description of the disorder in 1920, although by current diagnostic criteria his case would be highly atypical. A year later another German neurologist, A. Jakob described four cases, at least two of whom had clinical features suggestive of the entity today recognized as CJD.

Although CJD appears to occur as a predominantly sporadic disorder it can also occur as a dominantly inherited or infective condition. The latter mode of transmission was first elucidated during the study of kuru-kuru in the 1950's. This neurodegenerative condition occurs only in the people of the Fore region of Papua New Guinea and is thought to have resulted from the consumption of brains during endocannabalistic funeral rituals. The similarities between kuru-kuru and scrapie, the transmissible spongiform encephalopathy of sheep, prompted a veterinary neuropathologist, Hadlow, to suggest that transmission studies of kuru-kuru be performed. The success of those studies and the recognition that the neuropathological changes in kuru-kuru were similar to those of CJD, was followed by the transmission of CJD to the chimpanzee by intracerebral inoculation of brain tissue. In 1974 a case of iatrogenic CJD due to corneal transplantation occurred and subsequently contaminated neurosurgical instruments, dural grafts, and brain depth electrodes have all been recognized as transmitting the disease. In 1985 the first case was reported in a recipient of contaminated human derived growth hormone and subsequently over 60 similar cases have arisen world-wide in addition to 4 cases associated with human derived gonadotrophin. The familial occurrence of CJD has been recognized for many years but was unexplained. The discovery of linkage to a region on the short arm of chromosome 20 has led recently to the elucidation of various dominantly inherited mutations.

Variant Creutzfeldt-Jakob disease (vCJD) is a rare and fatal human neurodegenerative condition. Like Creutzfeldt-Jakob disease (CJD), vCJD is classified as a transmissible spongiform encephalopathy (TSE) because of characteristic spongy degeneration of the brain and the transmissibility of the disease. First described in March 1996, vCJD appears to be strongly linked to exposure to the BSE agent.

From October 1996 to early November 2000, 85 cases of vCJD have been reported in the United Kingdom, 3 in France and 1 in Ireland. Insufficient information is available at present to make any well-founded prediction about the future number.

The nature of the transmissible agent in CJD is the matter of some controversy. Previously considered a "slow virus" no viral agent has ever been convincingly demonstrated and no evidence of an immunological response seen. Additionally the infectious pathogen shows a remarkable resistance to treatments that would normally be expected to inactivate viruses. The viral hypothesis has been elegantly challenged by the prion ("proteinaceous infectious particle") theory which states that the infectious agent is derived from a protease-sensitive protein (designated $PrP^C$) which is a constituent of the normal cell membrane. It is postulated that the normal protein undergoes a post-translational conformational change forming the insoluble pathogenic form of the prion protein ($PrPS^{Sc}$). This in turn induces more of the normal $PrP^C$ to form $PrP^{Sc}$—hence a chain reaction is set in motion with the exponential production of the insoluble prion protein being formed. The initial abnormal prion protein needed to seed this process may occur spontaneously as a rare event (which would account for the low incidence of sporadic CJD), following inoculation (accounting for observed transmission phenomena) or when initiated by a genetic abnormality of the PrP gene. The mechanism by which PrP$^{Sc}$ induces the pathological changes in CJD-spongiform change, gliosis, neuronal loss and (infrequently) plaques remains unclear. Although the prion hypothesis neatly explains many of the observed phenomena of transmissible spongiform encephalopathies (TSEs) it has one particular weakness. Scrapie is known to exhibit various "strains" characterized by different incubation periods, clinical features and pathology when transmitted. This is much more in keeping with a virus-like agent and strain variation, independent of the host genome, is difficult to reconcile with the prion theory.

The majority of CJD-cases are sporadic (85%), between 10–15% are familial and the remainder are iatrogenic.

CJD occurs worldwide with a roughly even incidence of between 0.5–1.0 cases per million per year. Higher rates (up to 100-fold) have been reported in Slovakia and Libyan-born Israelis but this is explained by the high incidence of a certain mutation of the PrP gene in these groups. The geographical distribution of CJD in the United Kingdom over the past 25 years demonstrates no overall evidence of spatiotemporal aggregation of cases, despite the occurrence of local areas of relatively high incidence over short periods. There is no evidence of case to case transmission and spouses of sporadic cases do not have an increased incidence of the disease.

TSEs are known to affect various animal species including sheep, goats, mink, mule deer, cows and recently cats. Scrapie, a disorder of sheep and goats, has been known for over 300 years and is endemic in the British Isles. In 1938 experimental transfer of scrapie from one sheep to another by inoculation provided evidence of an infective etiology. However there is no evidence of transmission of scrapie from sheep to man and there is no increased incidence of CJD in countries with scrapie compared to those without (e.g. UK and Australia).

The close relationship in pathogenesis between BSE and CJD has in recent years triggered massive scientific and industrial research into further understanding disease transmission pathogenesis as well as into early diagnosis of the underlying disease.

Research, however, is hampered by the fact that both PrP$^C$, as well as PrP$^{Sc}$ are difficult to isolate, to purify and especially to handle. PrP is a fairly sticky protein. Moreover, PrP is a metastable protein with a pronounced tendency to aggregate or precipitate in physiological buffers. Aggregation and precipitation of PrP is frequently observed under long term storage conditions and can be induced or accelerated by increasing storage temperature.

What render PrP even more critical is the biohazards associated with handling a PrP from a biological source, especially with regard to disease transmission.

Various attempts to obtain a prion protein by recombinant expression are known from the literature. Hornemann, S., et al., FEBS Letters 413 (1997) 277–281, for example describe the expression of full-length murine prion protein (mPrP (23–231)). These researchers expressed the complete amino acid sequence of the prion protein, mPrP (23–231), in the cytoplasm of *Escherichia coli*. The corresponding protein has been obtained in the form of inclusion bodies, which had to be solubilized by 8 M urea and oxidatively refolded. The human prion protein has been expressed in *Escherichia coli* by Zahn, R., et al., FEBS Letters 417 (1997) 400–404. In this paper the human prion protein (hPrP) from amino acid 23 to amino acid 231 has been expressed, as well as several fragments of hPrP. These investigators used polypeptides comprising a histidine tail fusion protein. This did facilitate the purification of the proteins which also had been obtained in the form of inclusion bodies. When purified, isolated and stored in a rather concentrated solution the hPrP thus obtained has been found to be stable.

However, if used as a standard material for immunoassays, hPrP, has to be diluted to comparatively low concentrations and nonetheless the diluted material has to be stable for several months.

Physiological, buffered salt solutions that mimic the extracellular fluids of human tissues have uniformly failed to solubilize PrP in solution if stored for weeks or months at 4° C.

Immunoassays in general are performed at physiological pH. Hence polypeptides soluble at physiological buffer conditions are extensively used in various immunoassay methods, such as ELISA (enzyme-linked immunosorbent assay), for example in the diagnosis of and screening for a certain disease.

Due to its aggregation tendency under physiological buffer conditions, and due to its metastable nature the PrP is difficult to use in an immunoassay E.g., in a sandwich assay format PrP is difficult to handle, because it tends to aggregate or even precipitate. Due to its metastable nature PrP may also lead to false results caused by unspecific binding.

In addition the metastability of PrP under physiological buffer conditions renders this protein a difficult target for routine (bio-) chemical procedures. The vast majority of "labeling chemistries", i.e., the chemical procedures used for binding a label, e.g., a marker group to a polypeptide, are based on nucleophilic chemistry and thus rather restricted to a pH window from about pH 6 to about pH 8 and thus only work under more or less physiological buffer conditions. These routine procedures, e.g., as described in Aslam, M. and Dent, A., The preparation of protein-protein conjugates in "Bioconjugation", eds. M. Aslam and A. Dent, McMillan Reference, London (1998), pp. 216–363, are difficult to carry out with PrP.

Therefore a tremendous need exists to provide PrP in a thermodynamically stable rather than in its metastable form. In this thermodynamically stable form PrP is for example soluble at physiological pH, stable in solution and/or easier to produce and/or handle.

There is also an urgent need to provide such PrP without encountering the biohazards associated with PrP that has been isolated from a mammal.

SUMMARY

In one embodiment the invention is a complex which is soluble to at least 100 nM in a solution which has a pH of 7.4 and consists of 20 nM sodium phosphate and 150 nM sodium chloride. The complex comprises a prion protein (PrP), and a peptidyl prolyl isomerase chaperone, wherein the PrP and the peptidyl prolyl isomerase chaperone are covalently linked.

In another embodiment, the invention is a recombinant polypeptide which is soluble to at least 100 nM in a solution which has a pH of 7.4 and consists of 20 mM sodium phosphate and 150 mM sodium chloride. The recombinant polypeptide comprises a prion protein (PrP), a peptidic linker, and a peptidyl prolyl isomerase chaperone.

In yet another embodiment, the invention contemplates a recombinantly-produced fusion polypeptide. The fusion peptide comprises a prion protein (PrP), and an FKBP chaperone polypeptide selected from the group consisting of FkpA, Sly D, and trigger factor.

In yet another embodiment, the present invention is an expression vector. The expression vector comprises at least one nucleic acid sequence encoding a PrP, at least one nucleic acid sequence encoding FKBP chaperone selected from the group consisting of FkpA, SlyD and trigger factor, and a nucleic acid sequence encoding a peptidic linker.

In further embodiment, the present invention is a method for producing a soluble PrP-chaperone complex. The method includes incubating a polypeptide comprising a PrP covalently linked to a peptidyl prolyl isomerase chaperone in a buffer wherein both the PrP and the chaperone are solubilized. The method further includes adjusting the buffer to physiological conditions. The PrP-chaperone complex formed according to this method is soluble to at least 100 nM as measured in a solution which has a pH of 7.4 and consists of 20 mM sodium phosphate and 150 mM sodium chloride.

BRIEF DESCRIPTION OF THE DRAWINGS

FIG. 1: UV spectrum of the fusion protein SS-hPrP (23–230) after matrix-assisted refolding and imidazole step elution. The spectrum was recorded on a Uvicon XS photometer using a pathlength of 1 cm. Buffer conditions were 50 mM sodium phosphate pH 8.0, 100 mM sodium chloride and ~250 mM imidazole. The shape of the spectrum highlights the remarkable solubility of the chaperoned hPrP (23–230). Stray light effects which would indicate aggregation phenomena are not observed.

FIG. 2: Purification of SS-hPrP (23–230) as documented by SDS-PAGE. The Comassie-stained gel shows (from left to right) the protein standard M12 (Novagen), the *E. coli* crude extract, the IMAC flow-through, the imidazole eluate and the SS-hPrP (23–230) dimer fraction after gel filtration on a Superdex® 200 column.

FIG. 3: Differential CD-spectroscopy in the near UV region. Near UV CD spectra were recorded for the carrier module SS (thin line) and the fusion protein SSPrP (thick line). Subtraction of the SS spectrum from the SS-hPrP spectrum yields the broken thin line representing the CD signal contribution of the prion part of the fusion protein. When converted into mean residue weight ellipticity, a theoretical hPrP (23–230) spectrum results that is in good agreement with literature data. These results strongly suggest that SlyD (1–165) and human prion protein (23–230) behave as independent folding domains within the context of the fusion protein. Spectra were recorded on a Jasco-720 spectropolarimeter. The path length was 0.5 cm, the protein concentration of SS and SS-hPrp (23–230) was 33 μM, respectively. Buffer conditions were 50 mM NaP pH 7.8, 100 mM NaCl, 1 mM EDTA, the response was 2 s. The spectra have been accumulated (9×) to improve the signal-to-noise ratio.

FIGS. 4A and 4B: Different residual solubility of S-hPrP and SS-hPrP after long-term incubation at elevated temperatures. The two fusion proteins were incubated at varying temperatures (from top to bottom: 8° C., 35° C., 45° C., 50° C. and 55° C.) under identical buffer conditions and protein concentrations. Afterwards, they were assessed for aggregate formation by means of FPLC analysis on a Superdex®200 size exclusion column. FIG. 4A shows some aggregation tendency of S-hPrP at temperatures exceeding 45° C. The resulting aggregate particles do not elute from the column, but obviously interact with the Superdex matrix. In contrast, the recovery of SS-hPrP is very high (4B). Moreover, the aggregation tendency is significantly reduced in the twin carrier fusion construct, SS-hPrP.

FIG. 5: The chaperone carrier module SS significantly increases the thermo tolerance of human prion protein. SS-hPrP and S-hPrP were subjected to thermal unfolding (max. temp. 80° C.) and assessed for their solubility after cooling down to room temperature. Whereas S-hPrP elutes mainly as a high molecular aggregate (peak at 8.8 min), SS-hPrP elutes chiefly as a soluble dimer (peak at 13.15 min). The result clearly indicates that the SS carrier module increases the reversibility of thermally induced unfolding.

DETAILED DESCRIPTION OF THE DRAWINGS AND THE PRESENTLY PREFERRED EMBODIMENTS

It was the task of the present invention to investigate whether PrP can be provided in a form, which is both readily soluble under physiological buffer conditions and stable in solution even under long term storage conditions.

We found that folding helpers, e.g., many members of the peptidyl prolyl isomerase (PPI) class, especially from the FKBP family, not only exhibit catalytic activity, but also have substantial beneficial effects on the solubility of amyloidogenic proteins, or more generally speaking, of proteins which tend to aggregate, like the PrP. They do so by forming soluble complexes with such proteins that are otherwise (i.e. in an unchaperoned, isolated form) prone to aggregation. PrP which is both metastable and poorly soluble under physiological conditions turned out to be thermodynamically stable under mild physiological conditions (i.e. without the need for solubilizing additives such as detergents or chaotropic agents) once it is present as a complex with an appropriate PPI chaperone. Thus, for example we were able to produce soluble PrP-chaperone complexes comprising the prion protein (23–230)—which is otherwise prone to aggregation—and SlyD, FkpA or other FKBPs as solubility-conferring chaperones.

A soluble complex comprising a PrP and a PPI-class chaperone can for example be obtained from a single recombinant protein comprising both PrP and a PPI class chaperone. A recombinant protein comprising PrP and a chaperone selected from the peptidyl-prolyl-isomerase class of chaperones is described.

According to the procedure described here, it is now possible to provide a PrP in a readily soluble and stable form, e.g., for use as standard material in immunoassays.

The PrP-chaperone complexes described in the present invention provide a convenient means to produce a soluble and thermodynamically stable PrP for use in immunoassays irrespective of the detection format employed.

The novel complexes e.g., comprising PrP and SlyD, for example, are readily soluble, and thermodynamically stable under physiological conditions. They can be used to great advantage in the detection of PrP by immunological techniques or for immunization of laboratory animals with a PrP-PPI chaperone complex.

The present invention relates to a method for producing a soluble PrP-chaperone complex comprising a PrP covalently linked to a PPI chaperone, comprising: solubilizing said polypeptide, and adjusting the buffer to physiological conditions, wherein the PrP-chaperone complex formed is soluble to at least 100 nM as measured in a solution which has a pH of 7.4 and consists of 20 mM sodium phosphate and 150 mM sodium chloride.

A prion protein or "PrP" according to the present invention comprises amino acids 23–230 of the mouse or the human prion protein precursor. The sequence of the hPrP precursor is given in SEQ ID NO: 1.

In the following PrP is sometimes also referred to as "target protein".

It is obvious to the skilled artisan that PrP from non-human other mammalian species, as well as naturally occurring or synthetically produced variants of PrP may also be used with great advantage and shall also be encompassed by the present invention. The use of human PrP and naturally occurring variants thereof is most preferred.

A protein is considered "metastable" if it adopts different configurations in one and the same environment. For example PrP is metastable in a physiological buffer consisting of 20 mM sodium phosphate pH 7.4, 150 mM NaCl. Under long term storage conditions, even at 4° C., PrP tends to aggregate in such buffers or even precipitates from such buffers.

The PrP-chaperone complex according to the present invention, however, is "thermodynamically stable" in a buffer consisting of 20 mM sodium phosphate pH 7.4, 150 mM NaCl. In such a buffer the target protein PrP, as comprised in the PrP-PPI-chaperone complex, is readily soluble and is stable under long term storage conditions.

The term "complex" is used to indicate that the peptide domain corresponding to PrP and the peptide domain corresponding to the chaperone interact with each other whereby the chaperone confers a solubilizing effect on the PrP.

Production of the soluble chaperone-target protein complex starts from a solubilizing buffer condition, i.e. from a buffer in which both the target protein and the chaperone are soluble. An appropriate buffer, which may be termed "non-physiological" or "solubilizing" buffer, has to meet the requirement that both the target protein and the PPI chaperone are not denatured or at least not irreversibly denatured. Starting from such buffer conditions, the chaperone binds to the target protein, and a change of the buffer conditions from non-physiological to physiological conditions is possible without precipitation of the target protein.

An appropriate (non-physiological) buffer, i.e., a buffer in which both the target protein and the PPI-chaperone are soluble either makes use of high or low pH, or of a high chaotropic salt concentration or of a combination thereof.

Although a chaperone and a PrP can be used as separate polypeptides, we have observed that it is advantageous to link both proteins covalently. Such covalent linkage is possible by conventional chemical cross-linking procedures; preferably, however, the covalent linkage is achieved by producing a recombinant polypeptide comprising a PrP and a chaperone.

In a further preferred embodiment, the present invention relates to a process for the production of a soluble PrP-chaperone complex comprising the steps of solubilizing, under appropriate buffer conditions, a protein comprising a recombinantly linked PrP and a chaperone protein selected from the peptidyl prolyl isomerase class and thereafter adjusting the buffer to physiological conditions. In this manner an intramolecular complex is obtained which is soluble to at least 100 nM in a buffer which has a pH of 7.4 and consists of 20 mM sodium phosphate and 150 mM sodium chloride. It is most preferred to perform this process starting from so-called inclusion bodies.

In the case of the production of an intramolecular complex comprising a PPI-chaperone and PrP the solubilizing buffer preferably is a buffer with a rather high concentration of a chaotropic salt, e.g., 6.0 M guanidinium chloride at a pH of about 7.8. Upon renaturation the target protein assumes its native-like structure and a soluble intramolecular complex forms.

The present invention teaches the use of chaperones derived from the class of folding helpers termed peptidyl prolyl cis/trans isomerases (PPIs or PPIases) (cf. Dartigalongue, C., and Raina, S., Embo J. 17 (1998) 3968–3980). Well-known examples of this family are members called CypA, PpiD (Dartigalongue, C. and Raina, S., supra; Schmid, F. X., Molecular chaperones in the life cyle of proteins, eds. A. L. Fink and Y. Goto, Marcel Decker Inc., New York (1998), pp. 361–389), FkpA (Danese, P. N., et al., Genes Dev. 9 (1995) 387–398) and trigger factor (Crooke, E., and Wickner, W., Proc. Natl. Acad. Sci. USA 84 (1987) 5216–5220; Stoller, G., et al., Embo J. 14 (1995) 4939–4948).

The peptidyl prolyl isomerases are subdivided into three families, the parvulines (Schmid, F. X., supra; Rahfeld, J. U., et al., FEBS Lett. 352 (1994) 180–184) the cyclophilines (Fischer, G., et al., Nature 337 (1989) 476–478, and the FKBP family (Lane, W. S., et al., J. Protein Chem. 10 (1991) 151–160). The FKBP family exhibits an interesting biochemical feature: its members were originally identified by their ability to bind to macrolides, e.g., FK 506 and rapamycin (Kay, J. E., Biochem J. 314 (1996) 361–385).

Some prolyl isomerases comprise different subunits or modules having different functions, e.g., a module exhibiting catalytic activity and a module exhibiting the chaperone or binding activity. Such modular members of the FKBP family are FkpA (Ramm, K., and Pluckthun, A., J. Biol. Chem. 275 (2000) 17106–17113), SlyD (Hottenrott, S., et al., J. Biol. Chem. 272 (1997) 15697–15701) and trigger factor (Scholz, C., et al., Embo J. 16 (1997) 54–58). Preferably members of the FKBP family of the PPI class of chaperones are used.

It is also well known and appreciated that it is not necessary to always use the complete sequence of a molecular chaperone. Functional fragments of chaperones (so-called modules) which still possess the required abilities and functions may also be used (cf WO 98/13496).

For instance, FkpA is a periplasmic PPI that is synthesized as an inactive precursor molecule in the bacterial cytosol and translocated across the cytoplasmic membrane. The active form of FkpA (mature FkpA or periplasmic FkpA) lacks the signal sequence (amino acids 1 to 25) and thus comprises amino acids 26 to 270 of the precursor molecule. Relevant sequence information relating to FkpA can easily be obtained from public databases, e.g., from "SWISS-PROT" under accession number P 45523.

A close relative of FkpA, namely SlyD (Swiss Prot accession number P30856), consists of a structured N-terminal domain responsible for catalytic and chaperone functions and of a largely unstructured C-terminus that is exceptionally rich in histidine and cysteine residues (Hottenrott, S., et al., J. Biol. Chem. 272 (1997) 15697–15701). We found that a C-terminally truncated variant of SlyD comprising amino acids 1–165 efficiently exerts its solubilizing functions on PrP. Unlike in the wild-type SlyD, the danger of compromising disulfide shuffling is successfully circumvented in the truncated SlyD-variant (1–165) used. We find that SlyD can be even further truncated (1–148) without compromising the chaperone activity and thus the solubility-conferring features.

Variants of the above-mentioned chaperones, bearing one or several amino acid substitutions or deletions, may also be used to perform a process according to the present invention, as long as the solubilizing effect is conserved.

Of course, the present invention is not restricted to the use of the specifically mentioned members of the peptidyl prolyl isomerase class, but can also be performed using homologues thereof, i.e., chaperones of the same class of chaperones but derived from a different species of bacteria.

Appropriate chaperones from alternative sources, and appropriate fragments or mutants of PPI chaperones can be easily selected by using the procedures as described in the Examples. Preferred alternative sources for PPI chaperones are *Yersinia pestis*, *Vibrio cholerae*, *Pasteurella multocida*, and *Treponema pallidum*. We surprisingly found that for example C-terminally truncated SlyD homologues from *Y. pestis* (1–165), *V. cholerae* (1–157), *P. multocida* (1–156) and *T. pallidum* (1–160) share the same beneficial chaperone features despite considerable differences in amino acid sequence. Moreover, all of the aforementioned PPI chaperones prove to be well suited as carrier modules according to the invention described here.

In a preferred embodiment according to the present invention, a binding-competent PPIase chaperone is recombinantly linked to a PrP in a manner designed to yield a high expression rate of the gene product in the bacterial cytosol. A binding-competent PPIase as referred to in the present invention encompasses at least the functional unit that mediates binding to the PrP substrate (i.e. the substrate binding or chaperone motif), irrespective of its catalytic PPIase activity.

It is known (e.g., Scholz et al., supra) that modular PPIs preferentially bind to denatured or partially denatured proteins. PPIases have now been found to have the striking property of not only catalyzing the folding of proteins, but also of forming stable complexes with such proteins, thereby conferring solubility. Surprisingly the PPIases studied (such as TF, SlyD and FkpA) bind to and thus for example solubilize native-like PrP.

There is a wealth of information on complex formation between model biomolecules, e.g., between an antibody and an antigen (for review see Braden, B. C., and Poijak, R. J., Faseb J. 9 (1995) 9–16). Usually, complex formation and dissociation occur in parallel; the complex and the binding partners coexist in free equilibrium. Likewise, the same seems true for complexes between PPI chaperones and amyloidogenic proteins, like PrP, as described in the present invention.

The formation of a complex, as described in the present invention comprising a thermodynamically stable PrP, is especially important. Whereas PrP alone is known to be a metastable protein with poor solubility it has now been found to be readily soluble and stable, e.g., under physiological buffer conditions, in the complex with a PPI chaperone.

Antigens that are soluble and stable under long term storage conditions, e.g., under simple and well-defined buffer conditions such as phosphate buffered saline, are of tremendous advantage in diagnostic applications. They can be used directly, e.g., as standard material in an immunoassay. Long term storage conditions are understood as storage at 4 to 8° C. for 18 months. Usually liquid formulations of reagents used in immunoassays nowadays have to be stable under these conditions.

It is generally accepted that storage at elevated temperature for shorter periods of time is adequate to obtain a reasonable estimate of long term storage properties. As will be shown in the Examples section the PrP as comprised in a PrP-chaperone complex according to the present invention is clearly more stable than PrP alone.

Physiological buffer conditions are usually understood to correspond to salt and pH-conditions found in the plasma or serum of animals and are defined as a pH value of around 7.4 and a salt concentration of about 150 mM. The PrP-chaperone complex according to the present invention is readily soluble and thermodynamically stable under these buffer conditions. The PrP present therein is immunologically active, thus pointing to a native-like structure.

As the skilled artisan will appreciate the buffer conditions used for solubilization and renaturation may be modified as required and appropriate and must not be understood as an undue restriction of the invention, which can be carried out successfully over a broad range of buffer conditions.

The overall salt concentration of the physiological buffer is not critical as long as Prp is stabilized in its thermodynamically stable form. Preferably the physiological buffer comprises at least 10 mM of the buffer system and at most 200 mM. The other buffer constituents, if any, may be a salt without significant buffer capacity, e.g., sodium chloride. The physiological buffer preferably has a salt concentration between 20 and 500 mM, more preferably between 50 and 300 mM, and most preferably between 100 and 200 mM.

In a process according to the present invention, the physiological buffer may be varied to have a pH value in the range of 5.0 to 8.5; more preferably, the range of such buffer is between pH 5.5 and pH 8.3. Even more preferably, such physiological buffer conditions are defined as the salt concentrations stated above and a pH value between 6.0 and 8.0; most preferably, the pH of such a physiological buffer is between 6.5 and 7.8.

A preferred embodiment according to the present invention is a process for producing a soluble PrP-chaperone complex, comprising a PrP recombinantly linked to a peptidyl prolyl isomerase comprising: solubilizing said recombinant PrP-chaperone polypeptide and adjusting the buffer to physiological conditions. Whereas a PrP alone would spontaneously precipitate to a significant extent during this process, it surprisingly stays in solution when it is part of a recombinant protein according to the present invention. This important finding is most likely due to the formation of an intramolecular complex between PrP and the chaperone.

In the case of the recombinant production of PrP in *E. Coli*, the recombinantly produced PrP is preferably obtained in the form of inclusion bodies. This material is solubilized using a highly chaotropic reagent, e.g., 7.0 M guanidinium chloride. The PrP polypeptide is largely unstructured under these conditions. By changing the buffer in appropriate steps to physiological buffer conditions the PrP in solution assumes what is perceived as its native-like structure. Information on light-scattering particles (like aggregates) can easily be obtained from standard UV spectra.

It is important to emphasize the fact that the PrP within the PrP-chaperone complex according to the present invention adopts what is considered to be a native-like fold during transfer to physiological buffer conditions.

Preferably, the PrP-chaperone complex according to the present invention is characterized in that the PrP comprised therein is folded in a native-like manner. The native-like folded PrP within such a complex exhibits for example the required immunological or physical features.

Production of the soluble chaperone-PrP complex starts from non-physiological buffer conditions. The "non-physiological" buffer has to meet two requirements, that (a) unfolding of PrP is reversible to its native-like structure, and (b) the unfolding of the PPI-chaperone is reversible to its native-like structure. Starting from such buffer conditions, the chaperone binds to the amyloidogenic target protein, and a change of the buffer conditions from non-physiological to more or less physiological conditions is possible without precipitation of the polypeptide comprising the amyloidogenic PrP.

Whereas chaperones usually bind to denatured proteins and act upon them, thereby facilitating their correct (re-) folding, the situation on which the present invention is based is strikingly different. In contrast to the customary view of chaperone functions, in the inventive method the chaperone appears to bind to the native-like folded protein and to solubilize this protein under buffer conditions where PrP is otherwise metastable and aggregates and/or precipitates under long term storage conditions.

In a preferred embodiment according to the present invention, the PPI chaperone is selected from the group comprising FkpA, SlyD and trigger factor.

It has been found that especially FkpA or SlyD improve the solubility of PrP and form rather stable complexes therewith. A further preferred embodiment is therefore characterized in that the chaperone is selected from the group comprising FkpA and SlyD. Most preferably the chaperone SlyD is used to confer solubility on PrP.

As described further above, it is also possible to use fragments of chaperones to bring about the desired function. In case of the modular chaperones, like the FKBPs, comprising a catalytic module and a binding module, it is preferred that such a fragment at least comprises the binding domain, or that such fragment at least exhibits essentially a function comparable to the binding domain. A preferred functional fragment of a PPI-chaperone is for example EcSly D (1–165), i.e. the SlyD derived from $E.$ $coli$ and consisting of amino acids 1 to 165. It has been found that functional fragments of EcSlyD may even be shorter, e.g. only comprising amino acids 1 to 148 (=EcSlyD; 1–148). Preferably a functional fragment of EcSlyD comprises at least amino acids 1 to 148.

FKBP 12 is a human member of the FKBP family and essentially comprises the catalytic isomerase domain of a PPIase. Since it lacks an additional polypeptide-binding domain, it displays significantly reduced binding affinity towards unfolded or partially folded protein substrates as compared to other members of the FKBP family. It has been shown that unfolding and refolding of FKBP12 is a reversible process (Egan, D. A., et al., Biochemistry 32 (1993) 1920–1927; Scholz, C., et al., J. Biol. Chem. 271 (1996) 12703–12707). We find that refolding and unfolding of FkpA (25–270), EcSlyD (1–165), and EcSlyD (1–148) are also reversible thus fulfilling a pivotal requirement for the process described here.

A soluble PrP chaperone complex can also be prepared by mixing the PPI chaperone (e.g., produced by recombinant techniques) and PrP either obtained by conventional peptide synthesis or produced recombinantly. However, as described above, PrP is preferably and quite easily obtained in a soluble form by appropriate processing of a recombinant polypeptide comprising a PPI chaperone and PrP.

In a preferred embodiment, the present invention relates to a complex which is soluble to at least 100 nM in a solution which has a pH of 7.4 and consists of 20 mM sodium phosphate and 150 mM sodium chloride, comprising a PrP, and a peptidyl prolyl isomerase chaperone, wherein the PrP and the peptidyl prolyl isomerase chaperone are covalently linked.

It has been found that a ratio of 1:1 (PrP to PPI chaperone) is sufficient to form the soluble complex if both domains are covalently linked. Most advantageous molar ratios of PrP to chaperone are 1:1 and 1:2.

A soluble complex comprising a PrP and a PPI chaperone in a recombinantly linked form represents a very preferred embodiment according to the present invention.

A recombinant protein comprising at least one PrP domain and at least one PPI-chaperone domain can be transferred from non-physiological to physiological buffer conditions in different ways. Soluble intramolecular complexes between the PrP domain and for example the SlyD domain are easily obtained by adjusting the non-physiological buffer conditions to physiological buffer conditions by dialysis, rapid dilution or matrix-assisted refolding. Matrix-assisted re-folding represents a preferred method. The solution thus obtained, comprising the soluble PrP-chaperone complex can be directly used, e.g., for further modification or as standard material in an immunoassay.

Preferably the recombinant polypeptide according to the present invention comprises one PrP domain per chaperone domain. In yet another preferred embodiment the present invention relates to a recombinant protein comprising at least one PrP domain and at least two PPI-chaperone domains. Recombinant polypeptides comprising one PrP domain and two PPI-chaperones are also preferred. Most preferably the PPI chaperone of such recombinant polypeptide is N-terminal to the PrP.

The recombinant polypeptide used to obtain a soluble PrP-chaperone complex according to the present invention is expressed by means of standard techniques in molecular biology. Preferably the chaperone gene is incorporated in-frame upstream of the target protein gene into an expression vector comprising both the genetic information for PrP and the chaperone and optionally also the genetic information for an appropriate peptidic linker sequence. A preferred host for large-scale production of such a recombinant fusion protein is *E. coli.*

In a preferred embodiment, the present invention relates to a soluble complex comprising a PrP and a chaperone selected from the peptidyl prolyl isomerase class of chaperones. Most preferably the PPI chaperone part of the recombinant polypeptide lacks any export signal peptide (of the corresponding precursor molecule) and corresponds to the mature PPI chaperone. Since in this preferred embodiment the recombinant protein lacks a functional signal sequence, the gene product accumulates in the bacterial cytosol.

A striking feature of PrP as part of for example a recombinantly produced SlyD-PrP is its exceptional solubility compared to the "unchaperoned" PrP. It is interesting that the "chaotropic material" (i.e. SlyD-PrP in 6.0–7.0 M GuHCl) can be refolded in different ways, all resulting in a thermodynamically stable and soluble native-like form. Refolding is achieved in high yields, both by dialysis and by rapid dilution, as well as by renaturing size exclusion chromatography or matrix-assisted refolding. These findings suggest that in this covalently linked form, the PrP-SlyD fusion polypeptide is a thermodynamically stable rather than a metastable protein.

The recombinant SlyD-PrP polypeptide comprises two protein domains posing different folding requirements. Since the purification protocol includes an initial denaturation step, it is mandatory that the folding of the carrier chaperone is reversible. Indeed, there is compelling spectroscopic evidence for the reversible unfolding and refolding of both SlyD and PrP within the covalently linked protein complex.

Also preferred is a recombinant polypeptide which is soluble to at least 100 nM in a solution which has a pH of 7.4 and consists of 20 mM sodium phosphate and 150 mM sodium chloride, comprising a PrP, a peptidic linker, and a peptidyl prolyl isomerase chaperone.

The peptide linker sequence of such a recombinant polypeptide is designed to ensure optimal intramolecular association of the PrP and the chaperone domain used. Preferably, such a linker sequence is about 20 amino acids long and comprises amino acids supporting both flexibility and solubility such as glycine and serine. Preferably the linker is 10 to 50 amino acids in length. More preferably the length is 12 to 40 amino acids, and most preferably, the linker comprises 15 to 35 amino acids. Both the PrP and the chaperone are always in close proximity (fixed together, e.g., by an appropriate linker). In a preferred embodiment the recombinant polypeptide comprises mature FkpA or truncated SlyD (amino acids 1–165) linked to its target protein via a flexible linker. This, as the data indicate, has an additional stabilizing effect.

It has been surprisingly found that PrP, as part of the intramolecular complex between a PPI chaperone and PrP, is both soluble and stable. The improved stability of PrP in such a complex has additional advantages. For example, it is possible to obtain a fully renatured recombinant PrP-chaperone molecule very easily. The recombinant protein is initially solubilized by treatment with a chaotropic agent (e.g., guanidinium chloride). By simply passing the solubilized material over a gel filtration column, equilibrated with the appropriate physiological buffer, a fully renatured protein comprising the covalently linked protein domains can be obtained.

Matrix-assisted refolding can also be easily applied to great advantage, see Example 2 and FIG. 2. There it is shown that in a very convenient renaturation and easy purification step a soluble SlyD-SlyD-PrP fusion protein is obtained with a purity exceeding 90%.

It is a very important feature of the complex according to the present invention that the PrP within such a complex is present in a soluble form under physiological buffer conditions, e.g., at pH 7.4 in 20 mM phosphate 150 mM sodium chloride buffer. Unlike free PrP the PrP comprised in such a complex is neither sticky nor aggregation prone. This is a tremendous advantage for therapeutic as well as for diagnostic applications. In a preferred embodiment, the present invention relates to a composition of reagents that is soluble under physiological buffer conditions, comprising an intramolecular complex comprising a PrP and a chaperone selected from the peptidyl prolyl isomerase class of chaperones.

A soluble complex comprising native-like folded PrP and a chaperone selected from the peptidyl prolyl isomerase class of chaperones represents a very preferred embodiment of the present invention.

In terms of immunization with PrP, the progress made by providing a "soluble and native-like" PrP is quite obvious. For the first time soluble and native-like PrP is now available for injection under physiological buffer conditions.

In a preferred embodiment, the soluble complex as described is used to produce a composition of reagents for use as a medicament. The composition of reagents comprises the PrP-chaperone complex together with physiologically acceptable excipients and, where appropriate, suitable additives and/or conventional auxiliary substances.

It represents a further preferred embodiment according to the present invention to form a composition of reagents comprising a PrP-chaperone complex and to use such a composition for eliciting an immune response in a mammal. The novel immunogen is expected to induce a much broader immune response due to the special features of the chaperone carrier module.

With respect to diagnostic procedures, obvious advantages of a soluble PrP-chaperone complex according to the present invention are for example the increased stability of a PrP under physiological buffer conditions and/or higher diagnostic sensitivity and/or the increased numbers of conformational epitopes present (as compared to frequently used synthetic or recombinant peptide fragments), and/or the possibility to easily label the PrP-chaperone complex.

The complex can be labeled by selecting an appropriate method and strategy for chemical coupling as required. In the case of polypeptides, coupling chemistries targeting —SH, —$NH_2$ or —$COO^-$ residues as well as the —OH group of tyrosine, the imidazole group of histidine, or the heterocyclic imino groups of tryptophan are available. Several appropriate coupling chemistries are known for each of these functional groups (Aslam, M. and Dent, A., supra). Routine protein coupling chemistries require a protein to be soluble under the working buffer conditions, e.g., within a pH range of about 5 to 8.5.

Well-known labels are marker groups or effector groups, like solid phase binding groups. A labeled soluble PrP-chaperone complex represents a further preferred embodiment according to the present invention.

The labeling group can be selected from any known detectable marker groups, such as dyes, luminescent labeling groups such as chemiluminescent groups, e.g., acridinium esters or dioxetanes, or fluorescent dyes, e.g., fluorescein, coumarin, rhodamine, oxazine, resorufin, cyanine and derivatives thereof. Other examples of labeling groups are luminescent metal complexes, such as ruthenium or europium complexes, enzymes, e.g., as used for ELISA or for CEDIA (Cloned Enzyme Donor Immunoassay, e.g., EP-A-0 061 888), and radioisotopes.

Effector groups comprise, for example, one partner of a bioaffine binding pair. While performing an assay, the effector group interacts specifically and preferably non-covalently with the other partner of the bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g., steroid hormone receptor/steroid hormone. Preferred binding pair members comprise hapten, antigen and hormone. Especially preferred are haptens like digoxin and biotin and analogues thereof.

Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates, In: "Practice and theory of enzyme immunoassays", eds. R. H. Burdon and v. P. H. Knippenberg, Elsevier, Amsterdam (1990), pp. 221–278) and various volumes of "Methods in Enzymology", eds. S. P. Colowick, N. O. Caplan, Academic Press (1980)) dealing with immunological detection methods, especially volumes 70, 73, 74, 84, 92 and 121.

The present invention relates to the use of a soluble chaperone-PrP complex in an immunoassay. The soluble complex comprising PrP and a PPI chaperone is preferably used as a standard material in an immunoassay for detection of the PrP. In a further preferred embodiment, a labeled soluble complex comprising PrP and a PPI chaperone is used in an immunoassay for detection of antibodies to PrP.

It is state of the art to diagnose a TSE, e.g., BSE from brain tissue, by an immunoassay procedure. A key element of these assays is the proteolytic digestion of the sample, e.g., by proteinase K. Whereas $PrP^C$ is completely digested, $PrP^{Sc}$ is at least partially resistant and can be immunologically detected in a "digested sample". It is important to note that a PrP-PPI chaperone complex according to the present invention is digested in a manner comparable to $PrP^C$ from brain and thus can be used as an attractive alternative to $PrP^C$ from a natural source. Preferably it is used as a standard material replacing $PrP^C$ obtained from brain tissue.

The novel chaperone-PrP complex also the chaperone of such a complex to be derivatized and does not require the modification of the antigen (PrP) itself. It is generally accepted that modification of a polypeptide by a second chemical moiety, for example the coupling of a label to that molecule, is associated with a risk of negatively influencing the polypeptide. For example, the epitope under investigation may be compromised, or such labeling may cause non-specific binding. According to the present invention, it is now possible to derivatize specifically the chaperone within a chaperone-PrP complex.

Diagnostic reagents in the field of specific binding assays, like immunoassays, are usually best provided in the form of a kit, which comprises the specific binding agent or agents and the auxiliary reagents required to perform the assay. The present invention therefore also relates to an immunological kit comprising at least one composition of reagents comprising a PrP-chaperone complex according to the present invention and auxiliary reagents for performing a PrP measurement. Preferably the composition of reagents comprising the PrP-chaperone complex is provided in liquid form.

In another embodiment, a soluble complex comprising PrP and a PPI chaperone may also be used to elicit an immune response in a subject, such as a human or non-human animal. The soluble complexes may be administered to a subject in compositions, such as those that may contain an excipient or carrier. Such compositions may also include an adjuvant. Examples of conventional adjuvants include, but are not limited to, Freund's incomplete, Freund's complete, Merck 65, AS-2, alum, aluminum phosphate, mineral gels such as aluminum hydroxide, and surface active substances such as lysolecithin, pluronic polyols, polyanions, peptides, oil emulsions, keyhole limpet hemocyanin, and dinitrophenol. Other useful adjuvants include, but are not limited to, bacterial capsular polysaccharides, dextran, IL-12, GM-CSF, CD40 ligand, IFN-γ, IL-1, IL-2, IL-3, IL-4, IL-10, IL-13, IL-18 or any cytokine or bacterial DNA fragment.

One dose (administration) of a soluble complex composition may be given. However, one or more boosting doses, such as once, twice, three times or more may follow the first administration. The number of doses administered to a subject partly depends on the response of a subject to a soluble complex composition. Within the scope of the present invention, a suitable number of doses include any number required to immunize an animal with a soluble complex.

A second administration (booster) of the soluble complex composition may be given between about 7 days and 1 year after the first administration. The time between the first and second administrations may be 14 days to 6 months, 21 days to 3 months, and often between about 28 days and 2 months after the original administration. A third administration (second booster) may be given between about 14 days and 10 years after the first administration, e.g., between about 14 days and 3 years, often between about 21 days and 1 year, very often between about 28 days and 6 months after the first administration. Subsequent boosters may be administered at 2 week intervals, or 1 month, 3 month or 6 month to 10 year intervals.

Typically, an amount of soluble complex will be administered to a subject that is sufficient to immunize an animal against an antigen (i.e., an "immunologically effective dose" or a "therapeutically effective dose"). The amount required for an "immunologically effective dose" will depend in part on the weight and general state of health of the subject, and the judgment of the prescribing physician or other qualified personnel.

The effective dose of the soluble complex can be derived from animal models; such data can then be used to readily optimize administration to humans based on the animal data. A dose will typically be between about 1 fg and about 100 μg, often between about 1 pg and about 100 μg, more often between about 1 ng and about 50 μg, and usually between about 100 ng and about 50 μg. In some embodiments, the dose is between about 1 fg and about 100 μg per kg subject body weight, often between about 1 pg and about 100 μg, more often between about 1 ng and about 50 μg, and usually between about 100 ng and about 50 μg per kg subject body weight.

The soluble complex-containing compositions of the invention may be administered in a variety of ways and in various forms. A soluble complex composition may include carriers and excipients, such as buffers, carbohydrates, mannitol, proteins, polypeptides or amino acids such as glycine, antioxidants, bacteriostatic agents, chelating agents, suspending agents, thickening agents and/or preservatives; water, oils, saline solutions, aqueous dextrose and glycerol solutions, other pharmaceutically acceptable auxiliary substances as required to approximate physiological conditions, such as buffering agents, tonicity adjusting agents, wetting agents, etc. A conventional adjuvant may also be incorporated into the composition.

While any suitable carrier may be used to administer the compositions of the invention, the type of carrier will vary depending on the mode of administration. Compounds may also be encapsulated within liposomes. Biodegradable microspheres are convenient in some instances as carriers; for example, such as those described in U.S. Pat. No. 5,942,252.

Sterilization of the compositions is desirable, such as that accomplished by conventional techniques, such as sterile filtering. The resulting aqueous solutions may be packaged for use as is, or lyophilized.

The soluble complex compositions of the invention may be administered in a variety of ways, including by injection (e.g., intradermal, subcutaneous, intramuscular, intraperitoneal etc.), by inhalation, by topical administration, by suppository, by using a transdermal patch or by mouth.

When administration is by injection, compositions may be formulated in aqueous solutions, preferably in physiologically compatible buffers such as Hanks solution, Ringer's solution, 20 mM phosphate 150 mM sodium chloride buffer (pH 7.4), or physiological saline buffer. The solution may contain formulator agents such as suspending, stabilizing and/or dispersing agents. Alternatively, the composition may be in powder form for reconstitution with a suitable vehicle, e.g., sterile pyrogen-free water, before use. Inhalation-delivered compositions may be as aerosol sprays from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the proteins and a suitable powder base such as lactose or starch. For topical administration, the compositions may be formulated as solutions, gels, ointments, creams, suspensions, and the like, as are well known in the art. In some embodiments, administration is by means of a transdermal patch. Suppository compositions may also be formulated to contain conventional suppository bases.

When administration is oral, a composition can be readily formulated by combining the composition with pharmaceutically acceptable carriers. Solid carriers include mannitol, lactose, magnesium stearate, etc.; such carriers enable the formation of tablets, pills, dragees, capsules, liquids, gels, syrups, slurries, suspensions etc., for oral ingestion. Such formulations may be powders, capsules and tablets; suitable excipients include fillers such as sugars, cellulose preparation, granulating agents, and binding agents.

Methods of producing polyclonal and monoclonal antibodies, including binding fragments (e.g., F(ab)$_2$) and single chain versions are well known. However, many antigens are incapable of triggering an adequate antibody response. In one embodiment, a composition comprising a soluble complex of the invention and an antigen is administered to an animal, thus eliciting an immune response in the animal. Polyclonal or monoclonal antibodies are subsequently prepared by standard techniques.

Our data indicate that a complex comprising one or two SlyD chaperone carrier modules and one hPrP(23–230) should prove very useful as a diagnostic tool (e.g. as a protein standard). This complex will also be a potent immunogen enabling the induction of highly specific anti-hPrP antibodies.

The following examples, references, sequence listing and figures are provided to aid the understanding of the present invention, the true scope of which is set forth in the appended claims. It is understood that modifications can be made in the procedures set forth without departing from the spirit of the invention.

EXAMPLES

Example 1

Construction of an Expression Plasmid Comprising Tandem-EcSlyD and hPrP(23–230)

On the basis of the pET24a expression plasmid of Novagen (Madison, Wis., USA) the following cloning steps were performed. The vector was digested with NdeI and XhoI and a semi-synthetic cassette comprising tandem-EcSlyD (amino acids 1 to 165,) and hPrP(23–230) was inserted:

| NdeI | | | | | | BamHI | XhoI |
|---|---|---|---|---|---|---|---|
| | EcSlyD (1–165) | L | EcSlyD (1–165) | L | hPrP (23–230) | | |

L = (GGGS)$_5$GGG-Linker

This construct is simply referred to in the following text as SS-PrP. The insert of the resulting plasmid was sequenced (SEQ ID NO: 2) and found to encode the desired fusion protein (SEQ ID NO: 3), wherein the last 6 amino acids represent the hexa-His-tag derived from the expression system used. In this fusion protein the methionine in between the second linker and hPrP (23–230) and the amino acids LE at the end of hPrP have been introduced merely to facilitate cloning of hPrP (23–230).

Example 2

Purification of the SS-hPrP (23–230) Fusion Protein

E. coli BL21(DE3) cells harboring the expression plasmid according to example 1 were grown in LB medium plus kanamycin to an $OD_{600}$ of 1, and cytosolic overexpression was induced by adding isopropyl-β-D-thiogalactoside (IPTG) to a final concentration of 1 mM at a growth temperature of 37° C. 4 hours after induction, cells were harvested by centrifugation (20 min at 5000×g), frozen and stored at −20° C. For cell lysis, the frozen pellet was resuspended in 100 mM sodium phosphate pH 8.0, 7.0 M GuHCl, 10 mM imidazole at room temperature and the resulting suspension was stirred to complete cell lysis for two hours. After centrifugation and filtration, the lysate was applied to a Ni-NTA (nickel-nitrilo-triacetate) column pre-equilibrated in the aforementioned lysis buffer. After an intensive washing step (>20 column volumes of lysis buffer), the chaotropic lysis buffer was replaced by 50 mM sodium phosphate pH 7.8, 100 mM sodium chloride in order to allow the matrix bound protein to refold (at least 10 column volumes of refolding buffer were applied to make sure there was no residual GuHCl in chaotropic concentrations). The native fusion protein was eluted by applying an imidazole step of 500 mM in 50 mM sodium phosphate pH 7.8, 100 mM sodium chloride. Protein-containing fractions were assessed for purity (SDS-PAGE) and pooled. Finally, the protein was subjected to size exclusion chromatography and the dimer fraction was pooled, concentrated and assessed for its spectroscopic properties.

Example 3

UV-Spectroscopic Characterization of the Fusion Protein

Intriguingly, SS-hPrP(23–230) elutes as a soluble and native-like folded protein. The UV spectra of the recombinantly produced and matrix-refolded fusion protein do not indicate any aggregation tendency. As shown in FIG. 1, the baseline of the UV-absorption spectrum of SS-hPrp(23–230) in physiological buffer conditions almost equals the abscissa (beyond 310 nm), thus indicating that there are no light-straying particles resulting from self-association or aggregation phenomena.

Indeed, the shape of the spectrum depicted in FIG. 1 points to a soluble, easy-to-handle polypeptide fusion protein comprising hPrp(23–230). Thus the method described here facilitates the convenient recombinant production of a soluble form of the human prion protein in high amounts (yield>10 mg fusion protein/g wet weight) and in native-like conformation.

In contrast, PrP (23–230) alone displays a considerable aggregation tendency when refolded in the way described (spectra not shown). In our hands, PrP alone formed visible aggregates within hours when incubated in phosphate buffered saline.

The purity of the fusion polypeptide exceeds 90% after the simple two-step chromatography protocol described above (see FIG.: 2). It is noteworthy that comparable results have been found for S-hPrP (23–230). Thus, the twin chaperone carrier SS as well as the single carrier S confer a remarkable solubility on the human prion protein (23–230).

Example 4

CD-Spectroscopic Characterization of the Fusion Protein

In order to address the question as to whether hPrP (23–230) adopts a native-like fold within the fusion context, near-UV-CD spectra were recorded. Since CD signals in the near-UV region (260–320 nm) reflect an ordered molecular surrounding of aromatic residues, near-UV-CD spectra are a convenient means to characterize globularly folded proteins.

Both the carrier module SS and the complete fusion protein SS-hPrP (23–230) display characteristic CD-signals in the near-UV region (FIG.: 3). When the SS carrier signal is subtracted from the SS-hPrP (23–230) signal, the resulting spectrum strongly resembles the typical prion CD-spectra described in the literature (Hornemann et al., FEBS Lett. 413 (1997) 277–281). Thus, the result of this differential spectroscopy experiment provides compelling evidence that hPrP (23–230) is folded native-like in the fusion context (despite the presence of two covalently linked SlyD carrier units). This strongly suggests that the carrier module does not negatively affect the structural integrity of the human prion protein.

Example 5

The Chaperone Carrier Module Significantly Enhances the Thermo Tolerance of hPrP (23–230)

In order to address the question as to whether an additional carrier module might enhance the thermo tolerance (and thus increase the shelf life) of h-PrP(23–230), both SS-PrP and S-PrP were subjected to thermal stress under identical conditions. Afterwards, both fusion proteins were assessed for their residual solubility by means of FPLC analysis.

Indeed, we found pronounced differences between SS-hPrP and S-hPrP after long-time-incubation at elevated temperatures. When incubated overnight at temperatures above 50° C., S-hPrP precipitates almost quantitatively and there is virtually no more protein detectable in a gel filtration run on a Superdex® 200 column (FIG.: 4A). When, however, SS-hPrP is pretreated in the same way, the protein recovery after gel filtration is almost quantitative (FIG.: 4B). These findings strongly suggest that the chaperone carrier module SlyD (1–165) significantly increases the solubility of the target molecule hPrP(23–230), presumably by supporting the reversibility of thermally induced unfolding. They also point to the conclusion that the two carrier units in the fusion construct SS-hPrP do act cooperatively.

Figure 5:
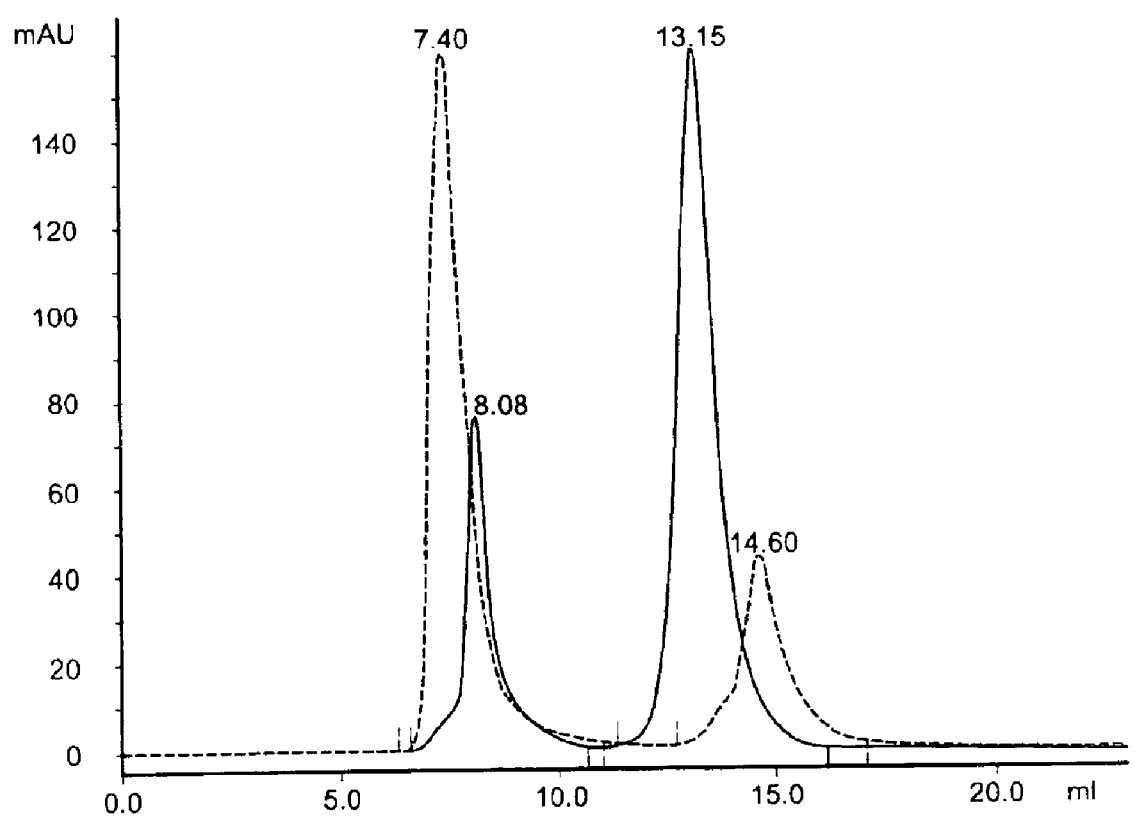

The solubilizing effect of the chaperone carrier is further highlighted after a short-term incubation at elevated temperature: Both SS-hPrP and S-PrP were subjected to thermal unfolding at identical protein concentrations (24 μM each) and buffer conditions. To this end, a 1 cm cuvette was placed in the thermostatable holder and the temperature was raised from 20° C. to 80° C. within a 1 hour run (1° C./min). After cooling down to room temperature, the samples were subjected to FPLC analysis as described and assessed for solubility. It turns out that the main part of S-hPrP elutes as a high molecular aggregate, whereas SS-hPrP elutes mainly as a soluble dimer (FIG. 5).

This constitutes a significant benefit of both S-hPrP and SS-hPrP as compared to the "unchaperoned" prion protein. In belief, the chaperone fusion constructs of hPrP(23–230) are superior to the unchaperoned protein with respect to thermal tolerance and solubility.

Example 6

Immunological Reactivity of SS-hPrP (23–230)

To determine the immunological activity of the fusion protein SS-hPrP(23–230), SS-PrP was tested in comparison to a commercially available recombinant PrP (Roboscreen, Leipzig, FRG) in a microtiter plate sandwich ELISA, using the biotinylated and POD-labelled monoclonal antibodies (Mabs) to PrP, Mab-ICSM18 and MAB-ICSM35, respectively, as described by White, C., et. al, Nature 422 (2003) 80–83.

Briefly, SS-PrP and recPrP were diluted to equimolar concentrations incubation buffer (PBS, pH 7.2, BSA, and preservatives). Protease inhibitor was added to one part of the dilutions.

Proteinase K digestion was carried out on each PrP dilution with a final concentration of 100 μg/ml for 40 minutes at 47° C. in the presence of 3 M guanidinium/HCl. The digestion was terminated by the addition of proteinase inhibitor at a final concentration of 10 mg/ml ELISA: 40 μl of the digested PrP dilutions were added per well of a flat bottomed and streptavidin-coated microtiter plate in quadruplets. 200 μl of Mab-Biotin and Mab-POD conjugate mixture were added per well. After incubating for 2 hours at room temperature, the plates were washed with PBS in the presence of 0.05% Tween20. 200 μl tetramethylbenzidine (TMB) substrate solution was added to each well. After incubation for a further 15 minutes at room temperature 5 μl stop solution (0.9 $NH_2SO_4$) was added. To determined the absorbance at 450 nm, the plate was measured in a microtiter plate reader (SLT).

TABLE 1

| | rec PrP [Absorbance] | SS-PrPc [Absorbance] |
|---|---|---|
| with protease inhibitor | 1.640 | 3.123 |
| without inhibitor | 0.050 | 0.075 |

Table 1 shows that under equimolar concentrations, SS-PrP is 2 times more reactive than the commercially available recombinant PrP. Furthermore the fusion protein SS-PrP is as sensitive to proteinase K digestion as the recombinant material. These data were confirmed several times and corroborate that SS-PrP should be a valuable tool for routine PrP assays.

Example 7

Stability of SS-hPrP (23–230)

SS-hPrP(23–230) and the commercially available rec PrP (Roboscreen) was diluted in lyophilisation buffer (8 mM Hepes, 40 mM NaCl, pH 7.5, in the presence of 1.6% BSA) to a final equimolar concentration of 60 ng/ml of PrP. After filtration through a 12 μm filter aliquots of the PrP dilutions were filled into vials, frozen with liquid nitrogen and lyophilized.

To determine the stability of PrP solutions, the lyophilised PrP samples were reconstituted like the biological samples with a four-fold volume of homogenisation buffer (20 mM Hepes, pH 7.5; in the presence of EDTA and sarcosyl) to yield a final PrP concentration of 15 ng/ml. Both reconstituted solutions of SS-PrP and of rec PrP were stored and stressed for 2 weeks at 4° C. and at 37° C., respectively.

After each week the PrP solutions were tested in the ELISA as described above and compared to a freshly reconstituted lyophilisate (100%).

TABLE 2

| | % Stability | | |
|---|---|---|---|
| | week 0 | week 1 | week 2 |
| rec PrP 4° C. | 100 | 99 | 93 |
| rec PrP 37° C. | 100 | 75 | 55 |
| SS-PrPc 4° C. | 100 | 99 | 89 |
| SS-PrPc 37° C. | 100 | 81 | 67 |

It is clear from Table 2 that the activity of both SS-hPrP and recPrP (Roboscreen) is reduced by no more than about 10% after two weeks storage at 4° C.

If the samples are stressed at 37° C., the stability of the fusion protein SS-PrP is improved PrP by about 10% compared to the stability of recombinant.

It is therefore intended that the foregoing detailed description be regarded as illustrative rather than limiting, and that it be understood that it is the following claims, including all equivalents, that are intended to define the spirit and scope of this invention.

LIST OF REFERENCES

Aslam, M. and Dent, A., The preparation of protein-protein conjugates in "Bioconjugation", eds. M. Aslam and A. Dent, McMillan Reference, London (1998), pp. 216–363

Braden, B. C., and Poijak, R. J., Faseb J. 9 (1995) 9–16

Colowick, S. P., and Caplan, N. O., Methods in Enzymology, Academic Press (1980)

Crooke, E., and Wickner, W., Proc. Natl. Acad. Sci. USA 84 (1987) 5216–5220

Danese, P. N., et al., Genes Dev. 9 (1995) 387–398

Dartigalongue, C., and Raina, S., Embo J. 17 (1998) 3968–3980

Egan, D. A., et al., Biochemistry 32 (1993) 1920–1927

EP-A-0061 888

Fischer, G., et al., Nature 337 (1989) 476–478

Glenner, G. G., and Wong, C. W., Biochem. Biophys. Res. Commun. 120 (1984) 885–890

Glenner, G. G., and Wong, C. W., Biochem. Biophys. Res. Commun. 122 (1984) 1131–1135

Hornemann, S., et al., FEBS Lett. 413 (1997) 277–281

Hottenrott, S., et al., J. Biol. Chem. 272 (1997) 15697–15701

Iwatsubo, T., et al., Neuron 13 (1994) 45–53

Kang, J., et al., Nature 325 (1987) 733–736

Kay, J. E., Biochem J. 314 (1996) 361–385

Lane, W. S., et al., J. Protein Chem. 10 (1991) 151–160

Masters, C. L., et al., Proc. Natl. Acad. Sci. USA 82 (1985) 4245–4249

Rahfeld, J. U., et al., FEBS Lett. 352 (1994) 180–184

Ramm, K., and Pluckthun, A., J. Biol. Chem. 275 (2000) 17106–17113

Roher, A. E., et al., Proc. Natl. Acad. Sci. USA 90 (1993) 10836–10840

Schmid, F. X., Molecular chaperones in the life cyle of proteins, eds. A. L. Fink and Y. Goto, Marcel Decker Inc., New York (1998), pp. 361–389

Scholz, C., et al., Embo J. 16 (1997) 54–58

Scholz, C., et al., J. Biol. Chem. 271 (1996) 12703–12707

Selkoe, D. J., et al., J. Neurochem. 46 (1986) 1820–1834

Selkoe, D. J., J. Neuropath. and Exp. Neurol. 53 (1994) 438–447

Selkoe, D. J., Neuron 6 (1991) 487

Stoller, G., et al., Embo J. 14 (1995) 4939–4948

SWISS-PROT, accession number P 45523

Tijssen, In: "Methods in Enzymology", eds. S. P. Colowick, N. O. Caplan, Academic Press (1980)

Tijssen, P., Preparation of enzyme-antibody or other enzyme-macromolecule conjugates, In: "Practice and theory of enzyme immunoassays", eds. R. H. Burdon and v. P. H. Knippenberg, Elsevier, Amsterdam (1990), pp. 221–278

Zahn, R., et. al., FEBS Lett. 417 (1997) 400–404

U.S. Pat. No. 5,942,252

White, C., et. al., Nature 422 (2003) 80–83

WO 98/13496

What is claimed is:

1. A protein which is soluble to at least 100 nM in a solution which has a pH of 7.4 and consists of 20 nM sodium phosphate and 150 nM sodium chloride, said protein comprising:
   a prion protein (PrP), and
   a peptidyl prolyl isomerase chaperone,
   wherein the PrP and the peptidyl prolyl isomerase chaperone are covalently linked.

2. The protein of claim 1, wherein the protein is soluble to at least 1 μM.

3. The protein of claim 1, wherein the PrP and the peptidyl prolyl isomerase chaperone are linked recombinantly.

4. The protein of claim 1, wherein the ratio of PrP to peptidyl prolyl isomerase chaperone is 1:1.

5. The protein of claim 1, wherein the ratio of PrP to peptidyl prolyl isomerase chaperone is 1:2.

6. The protein of claim 1, wherein the PrP is selected from the group consisting of mPRP and hPrP.

7. The protein of claim 1, wherein the peptidyl prolyl isomerase chaperone is an FKBP chaperone.

8. The protein of claim 7, wherein the FKBP chaperone is selected from the group consisting of SlyD, FkpA, and trigger factor.

9. The protein of claim 1, said protein further comprising a label.

10. An immunoassay reagent for the detection of PrP comprising the protein of claim 1 as a standard material.

11. A recombinant polypeptide which is soluble to at least 100 nM in a solution which has a pH of 7.4 and consists of 20 nM sodium phosphate and 150 nM sodium chloride, said recombinant polypeptide comprising:
a prion protein (PrP),
a peptidic linker, and
a peptidyl prolyl isomerase chaperone.

12. The recombinant polypeptide of claim 11, wherein the ratio of PrP to peptidyl prolyl isomerase chaperone is 1:1.

13. The recombinant polypeptide of claim 11, wherein ratio of PrP to peptidyl prolyl isomerase chaperone is 1:2.

14. The recombinant polypeptide of claim 11, wherein the PrP is selected from the group consisting of mPRP and hPrP.

15. The recombinant polypeptide of claim 11, wherein the peptidic linker is 10 to 50 amino acids in length.

16. The recombinant polypeptide of claim 11, wherein the peptidic linker is 15 to 35 amino acids in length.

17. The recombinant polypeptide of claim 11, wherein the peptidyl prolyl isomerase chaperone is an FKBP chaperone.

18. The recombinant polypeptide of claim 17, wherein the chaperone is selected from the group consisting of FkpA, SlyD, and trigger factor.

19. The recombinant polypeptide of claim 11, said recombinant polypeptide further comprising a label.

20. An immunoassay reagent for the detection of PrP comprising the recombinant polypeptide of claim 11 as a standard material.

21. A recombinantly-produced fusion polypeptide comprising:
a prion protein (PrP), and
an FKBP chaperone polypeptide, wherein said FKBP chaperone polypeptide is selected from the group consisting of FkpA, SlyD, and trigger factor.

22. The fusion polypeptide of claim 21, wherein the PrP is selected from the group consisting of mPRP and hPrP.

23. A recombinant polypeptide which is soluble to at least 100 nM in a solution which has a pH of 7.4 and consists of 20 nM sodium phosphate and 150 nM sodium chloride, said recombinant polypeptide comprising:
at least one PrP domain of a prion protein (PrP),
a peptidic linker, and
at least one chaperone domain of a peptidyl prolyl isomerase chaperone.

24. The recombinant polypeptide of claim 23, wherein the polypeptide comprises at least one PrP domain and at least two chaperone domains.

25. The recombinant polypeptide of claim 23, wherein the PrP is selected from the group consisting of mPRP and hPrP.

26. The recombinant polypeptide of claim 23, wherein the peptidic linker is 10 to 50 amino acids in length.

27. The recombinant polypeptide of claim 23, wherein the peptidic linker is 15 to 35 amino acids in length.

28. The recombinant polypeptide of claim 23, wherein the peptidyl prolyl isomerase chaperone is an FKBP chaperone.

29. The recombinant polypeptide of claim 28, wherein the chaperone is selected from the group consisting of FkpA, SlyD, and trigger factor.

30. The recombinant polypeptide of claim 23, said recombinant polypeptide further comprising a label.

31. An immunoassay reagent for the detection of PrP comprising the recombinant polypeptide of claim 23 as a standard material.

32. An expression vector comprising:
at least one nucleic acid sequence encoding a prion protein (PrP),
at least one nucleic acid sequence encoding a peptidic linker, and
at least one nucleic acid sequence encoding an FKBP chaperone selected from the group consisting of FkpA, SlyD, and trigger factor.

33. The expression vector of claim 32, wherein the nucleic acid sequence encoding FKBP chaperone is inserted in said expression vector upstream of the nucleic acid sequence encoding the peptidic linker and the nucleic acid sequence encoding a PrP.

34. An expression vector comprising:
at least one nucleic acid sequence encoding a prion protein (PrP),
at least one nucleic acid sequence encoding a peptidic linker, and
at least one nucleic acid sequence encoding a peptidyl prolyl isomerase chaperone.

35. The expression vector of claim 34, wherein the nucleic acid sequence encoding peptidyl prolyl isomerase chaperone is inserted in said expression vector upstream of the nucleic acid sequence encoding the peptidic linker and the nucleic acid sequence encoding a PrP.

36. An expression vector comprising:
at least one nucleic acid sequence encoding at least one PrP domain of a prion protein (PrP),
at least one nucleic acid sequence encoding a peptidic linker, and
at least one nucleic acid sequence encoding at least one chaperone domain of a peptidyl prolyl isomerase chaperone.

37. The expression vector of claim 36, wherein the nucleic acid sequence encoding at least one chaperone domain of the peptidyl prolyl isomerase chaperone is inserted in said expression vector upstream of the nucleic acid sequence encoding a peptidic linker and the nucleic acid sequence encoding a PrP domain of a PrP.

38. A method for producing a soluble prion protein (PrP)-chaperone protein comprising:
incubating a polypeptide comprising PrP covalently linked to a peptidyl prolyl isomerase chaperone in a buffer wherein both the PrP and the chaperone are solubilized to at least 100 nM, said buffer comprising a pH of 7.4, 20 mM sodium phosphate, and 150 mM sodium chloride.

39. The method of claim 38, wherein the polypeptide is solubilized with a chaotropic reagent.

40. The method of claim 39, wherein the chaotropic agent is 7.0 M guanidinium chloride.

41. The method of claim 38, wherein the PrP is produced recombinantly.

42. The method of claim 38, wherein the peptidyl prolyl isomerase chaperone is produced recombinantly.

43. The method of claim 38, wherein the PrP and the peptidyl prolyl isomerase chaperone are linked recombinantly.

44. The method of claim 38, wherein the PrP is selected from the group consisting of mPrP and hPrP.

45. The method of claim 38 wherein the peptidyl propyl isomerase chaperone is an FKBP chaperone.

46. The method of claim 38, wherein the peptidyl prolyl isomerase chaperone is a binding-competent fragment of the peptidyl prolyl isomerase chaperone.

47. The method of claim 38, wherein the peptidyl prolyl isomerase chaperone is of human origin.

48. The method of claim 38, wherein the peptidyl prolyl isomerase chaperone is derived from an organism selected from the group consisting of *Yersinia pestis, Vibrio cholerae, Pasteurelia multocida*, and *Treponema pallidum*.

49. The method of claim 38, wherein the peptidyl prolyl isomerase chaperone is an FKBP chaperone.

50. The method of claim 49, wherein the FKBP chaperone is selected from the group consisting of FkpA, SlyD, and trigger factor.

51. A method for eliciting an immune response in a subject comprising administering a composition comprising the protein of claim 1 to said subject, thereby eliciting antibodies in said subject, said antibodies having the ability to bind the PrP.

52. The method of claim 31, wherein the PrP is selected from the group consisting of mPrP and hPrP.

53. A method for eliciting an immune response in a subject comprising administering a composition comprising the recombinant polypeptide of claim 11 to said subject, thereby eliciting antibodies in said subject, said antibodies having the ability to bind the PrP.

54. The method of claim 53, wherein the PrP is selected from the group consisting of mPrP and hPrP.

55. A method for eliciting an immune response in a subject comprising administering a composition comprising the recombinant polypeptide of claim 23 to said subject, thereby eliciting antibodies in said subject, said antibodies having the ability to bind the PrP.

56. The method of claim 55, wherein the PrP is selected from the group consisting of mPrP and hPrP.

57. A method for producing antibodies to a prion protein (PrP) comprising administering the protein of claim 1 to an animal, thus eliciting an immune response in the animal, and isolating antibodies having the ability to bind the PrP.

58. The method of claim 57, wherein the antibody to PrP is a monoclonal antibody.

59. The method of claim 57, wherein the antibody to PrP is a polyclonal antibody.

60. A method for producing antibodies to prion protein (PrP) comprising administering the recombinant polypeptide of claim 11 to an animal, thus eliciting an immune response in the animal, and isolating antibodies having the ability to bind the PrP.

61. The method of claim 60, wherein the antibody to PrP is a monoclonal antibody.

62. The method of claim 60, wherein the antibody to PrP is a polyclonal antibody.

63. A method for producing antibodies to prion protein (PrP) comprising administering the recombinant polypeptide of claim 23 to an animal, thus eliciting an immune response in the animal, and isolating antibodies having the ability to bind the PrP.

64. The method of claim 63, wherein the antibody to PrP is a monoclonal antibody.

65. The method of claim 63, wherein the antibody to PrP is a polyclonal antibody.

* * * * *

UNITED STATES PATENT AND TRADEMARK OFFICE
CERTIFICATE OF CORRECTION

PATENT NO. : 7,094,757 B2
APPLICATION NO. : 10/745393
DATED : August 22, 2006
INVENTOR(S) : Elke Faatz et al.

It is certified that error appears in the above-identified patent and that said Letters Patent is hereby corrected as shown below:

On the Title Page

On page 2, in column 1, lines 24-25, under "OTHER PUBLICATIONS", delete "*Transactivatioin*" and substitute --*Transactivation*-- in its place.

On page 2, in column 1, line 26, under "OTHER PUBLICATIONS", immediately after "vol. 326" insert --,-- (comma).

On page 2, in column 1, line 51, before "*Virus Envelope*" delete "*Immunodificiency*" and substitute --*Immunodeficiency*"-- in its place.

On page 2, in column 2, line 9, delete "13363-1383" and substitute --13363-13383-- in its place.

On page 2, in column 2, line 25, after "in the life" delete "cyle" and substitute --cycle-- in its place.

On page 3, in column 1, line 2, before "*Structure on the Trigger Factor*" delete "*Molecular*" and substitute --*Modular*-- in its place.

On page 3, in column 1, line 11, after "Ellis, R.W." delete "(Chapter 29" and substitute --Chapter 29-- in its place.

On page 3, in column 1, line 23, delete "Cotents" and substitute --Contents-- in its place.

On page 3, in column 2, line 12, after "Mini-" delete "Tnhly" and substitute -- Tn*hly*-- in its place.

In the Claims

Column 30, delete claim 45 in its entirety.

Column 31, in claim 48, line 3, delete "*Pasteurelia*" and substitute --*Pasteurella*-- in its place.

Column 31, claims "46-49" should be renumbered as claims --45-48-- respectively.

UNITED STATES PATENT AND TRADEMARK OFFICE
CERTIFICATE OF CORRECTION

PATENT NO. : 7,094,757 B2
APPLICATION NO. : 10/745393
DATED : August 22, 2006
INVENTOR(S) : Elke Faatz et al.

It is certified that error appears in the above-identified patent and that said Letters Patent is hereby corrected as shown below:

In the Claims (cont'd)

Column 31, claim "50" should be renumbered as --49-- and in line 1 delete "claim 49" and substitute --claim 48-- in its place.

Column 31, claims "51" and "53" should be renumbered as --50-- and --52-- respectively.

Column 31, claim "52" should be renumbered as --51-- and in line 1 delete "claim 31" and substitute --claim 50-- in its place.

Column 31, claim "54" should be renumbered as --53-- and in line 1 delete "claim 53" and substitute --claim 52-- in its place.

Column 31, claim "55" should be renumbered as --54--.

Column 32, claim "56" should be renumbered as --55-- and in line 1 delete "claim 55" and substitute --claim 54-- in its place.

Column 32, claim "58" should be renumbered as --57-- and in line 1 delete "claim 57" and substitute --claim 56-- in its place.

Column 32, claim "59" should be renumbered as --58-- and in line 1 delete "claim 57" and substitute --claim 56-- in its place.

Column 32, claim "60" should be renumbered as --59--.

Column 32, claim "61" should be renumbered as --60-- and in line 1 delete "claim 60" and substitute --claim 59-- in its place.

Column 32, claim "62" should be renumbered as --61-- and in line 1 delete "claim 60" and substitute --claim 59-- in its place.

Column 32, claim "63" should be renumbered as --62--.

Column 32, claim "64" should be renumbered as --63-- and in line 1 delete "claim 63" and substitute --claim 62-- in its place.

UNITED STATES PATENT AND TRADEMARK OFFICE
CERTIFICATE OF CORRECTION

PATENT NO. : 7,094,757 B2
APPLICATION NO. : 10/745393
DATED : August 22, 2006
INVENTOR(S) : Elke Faatz et al.

It is certified that error appears in the above-identified patent and that said Letters Patent is hereby corrected as shown below:

In the Claims (cont'd)

Column 32, claim "65" should be renumbered as --64-- and in line 1 delete "claim 63" and substitute --claim 62-- in its place.

Signed and Sealed this

Twenty-second Day of May, 2007

JON W. DUDAS
*Director of the United States Patent and Trademark Office*

SEQUENCE LISTING

```
<160> NUMBER OF SEQ ID NOS: 3

<210> SEQ ID NO 1
<211> LENGTH: 208
<212> TYPE: PRT
<213> ORGANISM: Homo sapiens

<400> SEQUENCE: 1

Lys Lys Arg Pro Lys Pro Gly Gly Trp Asn Thr Gly Gly Ser Arg Tyr
1               5                   10                  15

Pro Gly Gln Gly Ser Pro Gly Gly Asn Arg Tyr Pro Pro Gln Gly Gly
            20                  25                  30

Gly Gly Trp Gly Gln Pro His Gly Gly Gly Trp Gly Gln Pro His Gly
        35                  40                  45
```

```
Gly Gly Trp Gly Gln Pro His Gly Gly Trp Gly Gln Pro His Gly
    50                  55                  60
Gly Gly Trp Gly Gln Gly Gly Thr His Ser Gln Trp Asn Lys Pro
65                  70                  75                  80
Ser Lys Pro Lys Thr Asn Met Lys His Met Ala Gly Ala Ala Ala
                85                  90                  95
Gly Ala Val Val Gly Leu Gly Gly Tyr Met Leu Gly Ser Ala Met
            100                 105                 110
Ser Arg Pro Ile Ile His Phe Gly Ser Asp Tyr Glu Asp Arg Tyr Tyr
        115                 120                 125
Arg Glu Asn Met His Arg Tyr Pro Asn Gln Val Tyr Tyr Arg Pro Met
130                 135                 140
Asp Glu Tyr Ser Asn Gln Asn Asn Phe Val His Asp Cys Val Asn Ile
145                 150                 155                 160
Thr Ile Lys Gln His Thr Val Thr Thr Thr Thr Lys Gly Glu Asn Phe
                165                 170                 175
Thr Glu Thr Asp Val Lys Met Met Glu Arg Val Val Glu Gln Met Cys
            180                 185                 190
Ile Thr Gln Tyr Glu Arg Glu Ser Gln Ala Tyr Tyr Gln Arg Gly Ser
        195                 200                 205

<210> SEQ ID NO 2
<211> LENGTH: 1761
<212> TYPE: DNA
<213> ORGANISM: Artificial Sequence
<220> FEATURE:
<223> OTHER INFORMATION: Nucleic acid sequence coding for a fusion
      protein

<400> SEQUENCE: 2
catatgaaag tagcaaaaga cctggtggtc agcctggcct atcaggtacg tacagaagac    60
ggtgtgttgg ttgatgagtc tccggtgagt gcgccgctgg actacctgca tggtcacggt   120
tccctgatct ctggcctgga aacggcgctg aaggtcatg aagttggcga caaatttgat    180
gtcgctgttg gcgcgaacga cgcttacggt cagtacgacg aaaacctggt gcaacgtgtt   240
cctaaagacg tatttatggg cgttgatgaa ctgcaggtag gtatgcgttt cctggctgaa   300
accgaccagg gtccggtacc ggttgaaatc actgcggttg aagacgatca cgtcgtggtt   360
gatggtaacc acatgctggc cggtcagaac ctgaaattca acgttgaagt tgtggcgatt   420
cgcgaagcga ctgaagaaga actggctcat ggtcacgttc acgcgcgcgc acgatcacca   480
cacgatcacg accacgacgg tggcggttcc ggcggtggct ctggtggcgg aagcggtggc   540
ggttccggcg gtggctctgg tggcggtaaa gtagcaaaag acctggtggt cagcctggcc   600
tatcaggtac gtacagaaga cggtgtgttg ttgatgagt ctccggtgag tgcgccgctg    660
gactacctgc atggtcacgg ttccctgatc tctggcctgg aaacggcgct ggaaggtcat   720
gaagttggcg acaaatttga tgtcgctgtt ggcgcgaacg acgcttacgg tcagtacgac   780
gaaaacctgg tgcaacgtgt tcctaaagac gtatttatgg gcgttgatga actgcaggta   840
ggtatgcgtt tcctggctga aaccgaccag ggtccggtac cggttgaaat cactgcggtt   900
gaagacgatc acgtcgtggt tgatggtaac cacatgctgg ccggtcagaa cctgaaattc   960
aacgttgaag ttgtggcgat cgcgaagcg actgaagaag aactggctca tggtcacgtt   1020
cacgcgcgcg acgatcacca ccacgatcac gaccacgacg gtggcggttc cggcggtggc   1080
tctggtggcg gatccggtgg cggttccggc ggtggctctg gtggcggtat gaaaaaacgc   1140
```

```
ccaaaaccgg gtggctggaa cactgggggc agccgctatc ctggccaggg ctcgccggga    1200
gggaatcgtt acccaccaca gggtggtggg ggctggggtc agccgcacgg cggcggttgg    1260
gggcaaccgc atggcggcgg atggggtcaa cctcacgggg gaggctgggg ccaaccgcat    1320
ggtggtgggt ggggtcaggg aggcggtacg cattcccaat ggaacaaacc gagtaaaccc    1380
aaaaccaaca tgaagcatat ggcgggtgcc gctgccgcag gtgcagttgt cggtggcctg    1440
ggcggctaca tgttaggaag cgcgatgtca agacccatta tccattttgg ctctgactat    1500
gaagatcgtt actaccgcga gaatatgcac cgttatccga atcaggtgta ttatcgtccg    1560
atggatgaat acagcaacca gaataacttc gtccacgact gtgttaatat taccattaag    1620
cagcatacag tgacgacaac cacgaaaggt gaaaacttta ccgagaccga tgtgaaaatg    1680
atggaacgag tagtagaaca aatgtgcatc actcagtacg aacgcgagag tcaggcgtat    1740
tatcagcggg gctcgctcga g                                              1761

<210> SEQ ID NO 3
<211> LENGTH: 592
<212> TYPE: PRT
<213> ORGANISM: Artificial Sequence
<220> FEATURE:
<223> OTHER INFORMATION: Amino acid sequence of a fusion protein

<400> SEQUENCE: 3

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
        115                 120                 125

Asn Leu Lys Phe Asn Val Glu Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Ser Gly Gly Gly Ser Gly Gly Gly
                165                 170                 175

Ser Gly Gly Gly Ser Gly Gly Gly Ser Gly Gly Gly Lys Val Ala Lys
            180                 185                 190

Asp Leu Val Val Ser Leu Ala Tyr Gln Val Arg Thr Glu Asp Gly Val
        195                 200                 205

Leu Val Asp Glu Ser Pro Val Ser Ala Pro Leu Asp Tyr Leu His Gly
    210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
```

-continued

```
                        245                 250                 255
Gln Tyr Asp Glu Asn Leu Val Gln Arg Val Pro Lys Asp Val Phe Met
                260                 265                 270
Gly Val Asp Glu Leu Gln Val Gly Met Arg Phe Leu Ala Glu Thr Asp
                275                 280                 285
Gln Gly Pro Val Pro Val Glu Ile Thr Ala Val Glu Asp Asp His Val
                290                 295                 300
Val Val Asp Gly Asn His Met Leu Ala Gly Gln Asn Leu Lys Phe Asn
305                 310                 315                 320
Val Glu Val Val Ala Ile Arg Glu Ala Thr Glu Glu Glu Leu Ala His
                    325                 330                 335
Gly His Val His Gly Ala His Asp His His Asp His Asp His Asp
                340                 345                 350
Gly Gly Gly Ser Gly Gly Gly Ser Gly Gly Ser Gly Gly Gly Ser
                355                 360                 365
Gly Gly Gly Ser Gly Gly Gly Met Lys Lys Arg Pro Lys Pro Gly Gly
                370                 375                 380
Trp Asn Thr Gly Gly Ser Arg Tyr Pro Gly Gln Gly Ser Pro Gly Gly
385                 390                 395                 400
Asn Arg Tyr Pro Pro Gln Gly Gly Gly Trp Gly Gln Pro His Gly
                    405                 410                 415
Gly Gly Trp Gly Gln Pro His Gly Gly Gly Trp Gly Gln Pro His Gly
                420                 425                 430
Gly Gly Trp Gly Gln Pro His Gly Gly Gly Trp Gly Gln Gly Gly Gly
                435                 440                 445
Thr His Ser Gln Trp Asn Lys Pro Ser Lys Pro Lys Thr Asn Met Lys
450                 455                 460
His Met Ala Gly Ala Ala Ala Ala Gly Ala Val Val Gly Gly Leu Gly
465                 470                 475                 480
Gly Tyr Met Leu Gly Ser Ala Met Ser Arg Pro Ile Ile His Phe Gly
                    485                 490                 495
Ser Asp Tyr Glu Asp Arg Tyr Tyr Arg Glu Asn Met His Arg Tyr Pro
                500                 505                 510
Asn Gln Val Tyr Tyr Arg Pro Met Asp Glu Tyr Ser Asn Gln Asn Asn
                515                 520                 525
Phe Val His Asp Cys Val Asn Ile Thr Ile Lys Gln His Thr Val Thr
                530                 535                 540
Thr Thr Thr Lys Gly Glu Asn Phe Thr Glu Thr Asp Val Lys Met Met
545                 550                 555                 560
Glu Arg Val Val Glu Gln Met Cys Ile Thr Gln Tyr Glu Arg Glu Ser
                    565                 570                 575
Gln Ala Tyr Tyr Gln Arg Gly Ser Leu Glu His His His His His His
                580                 585                 590
```